United States Patent
Jindo et al.

(10) Patent No.: US 9,556,410 B2
(45) Date of Patent: Jan. 31, 2017

(54) HOMOGENIZER AND STORAGE COOLER

(71) Applicant: Sysmex Corporation, Kobe-shi, Hyogo (JP)

(72) Inventors: Katsuhiko Jindo, Kobe (JP); Yoshinori Ooi, Kobe (JP); Shoichiro Asada, Kobe (JP); Daijyu Obinata, Shiojiri (JP); Keiichiro Shohmi, Kobe (JP)

(73) Assignee: Sysmex Corporation, Hyogo (JP)

( * ) Notice: Subject to any disclaimer, the term of this patent is extended or adjusted under 35 U.S.C. 154(b) by 783 days.

(21) Appl. No.: 13/851,549

(22) Filed: Mar. 27, 2013

(65) Prior Publication Data

US 2013/0258800 A1    Oct. 3, 2013

(30) Foreign Application Priority Data

Mar. 29, 2012  (JP) .................................. 2012-076232
Feb. 27, 2013  (JP) .................................. 2013-037906

(51) Int. Cl.
| | | |
|---|---|---|
| B01F 15/06 | (2006.01) | |
| C12M 1/33 | (2006.01) | |
| B01F 13/10 | (2006.01) | |
| C12M 1/00 | (2006.01) | |

(52) U.S. Cl.
CPC .......... *C12M 45/02* (2013.01); *B01F 13/1022* (2013.01); *B01F 13/1041* (2013.01); *B01F 15/065* (2013.01); *C12M 47/08* (2013.01); *C12M 47/20* (2013.01)

(58) Field of Classification Search
CPC . B01F 15/065; B01F 13/1022; B01F 13/1041; C12M 45/02; C12M 47/20; C12M 47/08

USPC ................................ 366/197–207; 435/306.1
See application file for complete search history.

(56) References Cited

U.S. PATENT DOCUMENTS

| | | | |
|---|---|---|---|
| 4,307,846 A * | 12/1981 | Spelsberg ........... | B02C 19/0056 241/169.1 |
| 4,509,695 A | 4/1985 | Bessman | |
| 5,390,859 A | 2/1995 | Rajasekaran | |
| 6,994,827 B2 * | 2/2006 | Safir ....................... | B01F 7/167 222/252 |
| 7,370,819 B2 * | 5/2008 | Czarnek ................ | G01N 1/286 241/169.1 |
| 8,216,528 B2 | 7/2012 | Shomi | |

(Continued)

FOREIGN PATENT DOCUMENTS

| | | |
|---|---|---|
| CN | 1724133 A | 1/2006 |
| CN | 102288462 A | 12/2011 |

(Continued)

OTHER PUBLICATIONS

Extended European Search Report for European Application No. 13161058.6, dated Aug. 22, 2013, 4 pages.

*Primary Examiner* — Charles Cooley
(74) *Attorney, Agent, or Firm* — Brinks Gilson & Lione

(57) ABSTRACT

A homogenizer, for homogenizing a tissue sample collected from a living body, comprising: a main body; and a storage cooler, comprising a container holder for holding a sample container, configured to cool a tissue sample in the sample container held by the container holder, the storage cooler being detachably installed to the main body, wherein the main body has a blender for crushing the tissue sample in the sample container held in the storage cooler is disclosed.

17 Claims, 22 Drawing Sheets

(56) References Cited

U.S. PATENT DOCUMENTS

| | | | | |
|---|---|---|---|---|
| 8,438,971 B1* | 5/2013 | Thurley | ............... | A47J 43/044 366/146 |
| 2006/0011755 A1* | 1/2006 | Ando | ....................... | B01F 3/12 241/1 |
| 2006/0030796 A1 | 2/2006 | Xu et al. | | |
| 2006/0044935 A1* | 3/2006 | Benelli | ................ | A47J 27/004 366/145 |
| 2006/0260423 A1* | 11/2006 | Sekizawa | ............. | B01F 1/0011 |
| 2007/0069054 A1* | 3/2007 | Shomi | ................... | C12M 45/02 241/199 |
| 2010/0107752 A1* | 5/2010 | Fernando | ............... | B01F 7/161 |
| 2011/0186672 A1* | 8/2011 | Bougy | ................. | B01F 7/1605 241/277 |
| 2012/0109567 A1* | 5/2012 | Bobasheva | .............. | B01F 7/18 |
| 2013/0258800 A1* | 10/2013 | Jindo | ..................... | C12M 45/02 366/144 |
| 2014/0056783 A1* | 2/2014 | Jindo | ...................... | G01N 1/28 422/536 |

FOREIGN PATENT DOCUMENTS

| | | | |
|---|---|---|---|
| DE | 102012020038 A1 * | 4/2014 | |
| EP | 1 616 618 A2 | 1/2006 | |
| EP | 1 616 618 A3 | 1/2006 | |
| EP | 1616618 B1 | 4/2009 | |
| JP | 04346741 A * | 12/1992 | |
| JP | 2003-315223 A | 11/2003 | |
| JP | 2006-122888 A | 5/2006 | |
| JP | 2006-320888 A | 11/2006 | |
| JP | 2008-521607 A | 6/2008 | |
| JP | 2008-259489 A | 10/2008 | |
| WO | WO 2004/073846 A1 | 9/2004 | |
| WO | WO 2006/060566 A2 | 6/2006 | |
| WO | WO 2006/060566 A3 | 6/2006 | |

* cited by examiner

HOMOGENIZER AND STORAGE COOLER

RELATED APPLICATIONS

This application claims priority under 35 U.S.C. §119 to Japanese Patent Application Nos. 2012-076232 filed on Mar. 29, 2012 and 2013-037906 filed on Feb. 27, 2013, the entire contents of which are hereby incorporated by reference.

BACKGROUND OF THE INVENTION

1. Field of the Invention

The present invention relates to an automated homogenizer for homogenizing a tissue sample collected from a human, animal, or plant, and a storage cooler used by the homogenizer.

2. Description of the Related Art

Genetic testing has spread rapidly in recent years in the field of clinical diagnosis. Genetic tests are test for the clinical purpose of identifying the presence or absence of mutations or karyotypes related to genetic diseases by analyzing nucleic acids and chromosomes. As an example of genetic testing, nucleic acids associated with cancers are amplified and examined to determine whether cancer cells are contained within tissue excised from a living body. This examination process is mainly three processes of preprocessing, nucleic acid amplification, and detection.

The preprocessing is a homogenization process to homogenize tissue. The homogenization process uses a homogenization method employing a so-called blender homogenizing tool, ultrasound homogenizing method, pressure homogenizing method or the like. Among such several types of methods, the method using a blender has a problem, that is, inasmuch as the temperature of the tissue is elevated due to the heat generated by friction between the tissue and the homogenizing tool, or heat generated within the homogenizing tool occurs in the blender operation. There is concern that the proteins contained in the tissue will be thermally denatured and prevent accurate measurement when the temperature of the tissue increases. Therefore, it is suggested that the tissue is cooled within a test tube while be homogenized.

Japanese Laid-Open Patent Application No. 2006-320888 discloses a homogenizer configured to cool a pulverizer container that contains a tissue to be pulverized and a pulverizing medium. This homogenizer houses a homogenizer container intermediated by thermally conductive resin within a cooling container formed in a dual structure, and is configured to cool the homogenizer container by circulating coolant around the cooling container.

The tissue must be cooled from the time the tissue is collected from a living being until the homogenizing process is performed and not only during the homogenizing process in order to avoid elevating the tissue temperature to room temperature so as to suppress thermal denaturation of the tissue and obtain accurate measurements. The homogenizer disclosed in Japanese Laid-Open Patent Application No. 2006-320888 requires that a bowl and ice are prepared beforehand to cool the container prior to the homogenizing process separately from the cooling medium used to cool the container that contains the tissue during the homogenizing process. The operator also must move the specimen from the bowl to the homogenizer when the precooled container is installed in the homogenizer.

SUMMARY OF THE INVENTION

A first aspect of the present invention is a homogenizer, for homogenizing a tissue sample collected from a living body, comprising: a main body; and a storage cooler, comprising a container holder for holding a sample container, configured to cool a tissue sample in the sample container held by the container holder, the storage cooler being detachably installed to the main body, wherein the main body has a blender for crushing the tissue sample in the sample container held in the storage cooler.

A second aspect of the present invention is a homogenizer, for homogenizing a tissue sample collected from a living body, comprising: an installation section for installing a storage cooler used to hold and cool a sample container containing a tissue sample, a blender for homogenizing the tissue sample in the sample container held in the storage cooler installed on the installation section; a moving section configured to move the installation section between an installing position at which the user installs the storage cooler on the installation section, and a homogenizing position at which the blender accesses in the sample container held by the storage cooler to homogenizes a tissue sample.

A third aspect of the present invention is a homogenizer, for homogenizing a tissue sample collected from a living body, comprising: a storage cooler including a container holder for holding a sample container with cooling, and a main body on which the storage cooler is detachably equipped, wherein the main body includes: a blender that homogenizes a tissue sample in the sample container held by the container holder; a detector that detects the equipped storage cooler; an instruction receiver that receives an instruction to start a homogenization; and a controller for controlling the operation of the blender, the controller disallows an execution of the homogenization when the detector does not detects the equipped storage cooler, even if the instruction to start is received.

A fourth aspect of the present invention is a storage cooler detachably installed in a homogenizer for homogenizing a tissue sample collected from a living body, comprising: a holding section for holding a sample container containing a tissue sample; and a cooling section for cooling the sample container held by the holding section.

DETAILED DESCRIPTION OF THE PREFERRED EMBODIMENTS

The preferred embodiments of the present invention are described hereinafter with reference to the drawings.

First Embodiment

Structure of the Homogenizer

Figure 1:
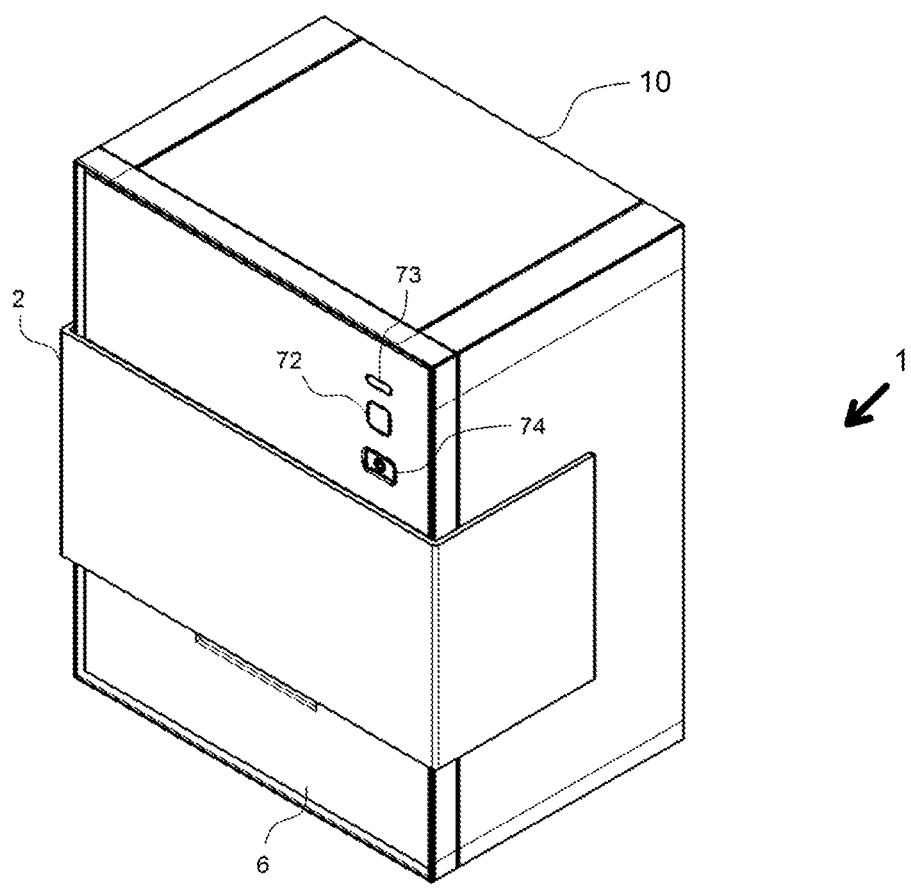
FIG. 1 is a perspective view showing the outward appearance of an embodiment of the homogenizer.

FIG. 1 is a perspective view showing the outward appearance of an embodiment of the homogenizer. The homogenizer 1 of the present embodiment is mainly installed in a laboratory at hospitals to homogenize tissue collected from patients in the operating room. The homogenizer 1 is an automated homogenizer to homogenize tissue in a buffer solution with a blender. The homogenizer 1 is provided with an essentially rectangular main body 10, and storage cooler (refer to FIG. 2) that is removable from the main body. The main body 10 is provided with a cover 2 that covers part of the front surface. The cover 2 is configured to slide vertically so as to open and close. FIG. 1 shows the cover 2 in the closed state.

Figure 2:
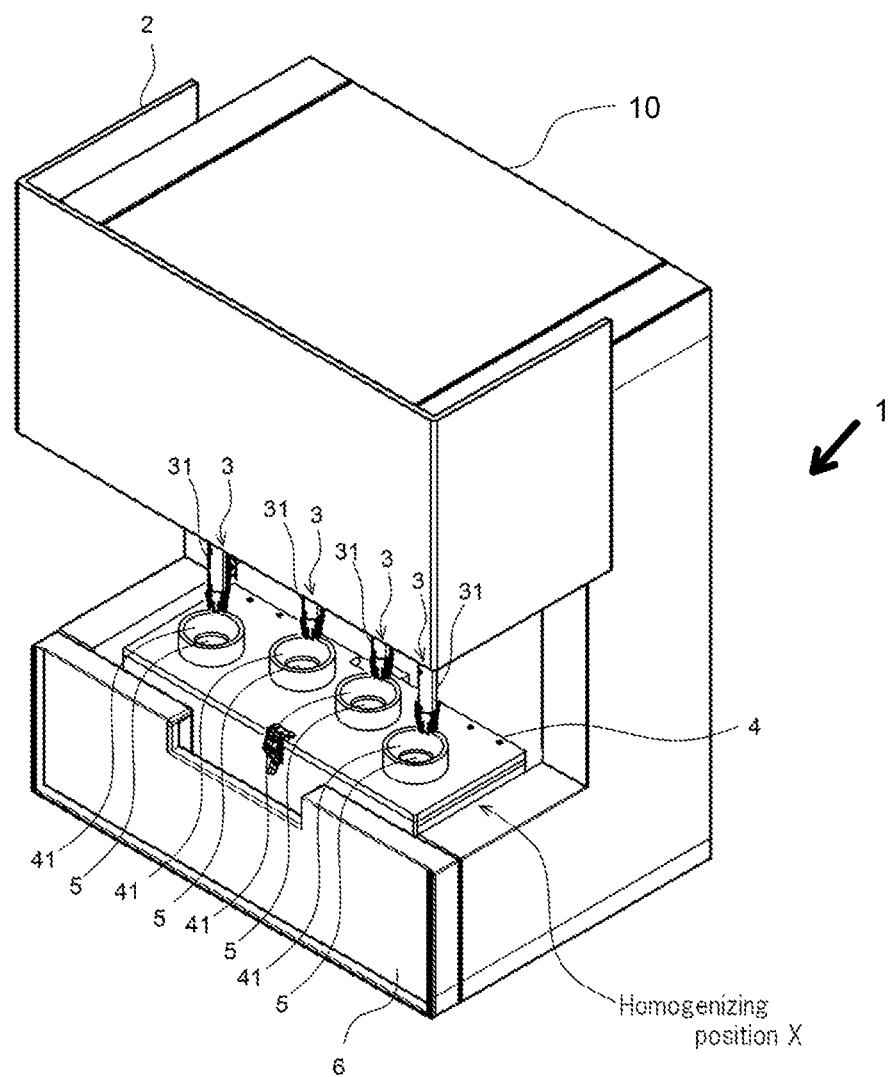
FIG. 2 is a perspective view showing the outward appearance of the homogenizer with the cover open.

When the cover 2 is closed then slidably moved upward, the cover 2 attains the open state. FIG. 2 is a perspective view showing the outward appearance of the main body 10 with the cover 2 in the open state. When the cover 2 is open, the central part in the vertical direction of the main body 10 is exposed. The central part is hollow in the front side, and the hollow part is provided with four homogenizing sections 3. The homogenizing section 3 has a rotation mechanism provided in the hollow part of the top section, and a blender 31 as a homogenizing tool used to pulverize the tissue. The blender 31 is disposable to prevent contamination, and can be removed from the rotating mechanism.

The blender 31 is a plastic member that is roughly cylindrical, and the tip is mounted on the rotating mechanism. The blender 31 is thus mounted on the rotating mechanism so as to hang down from the hollow top section. The blender 31 has a double structure, each cylindrical with an inner side and an outer side. The bottom end of the respective inner part and the outer part has a blade to pulverize the tissue. The rotation mechanism has an internal brushless DC blade rotation motor 32 (refer to FIG. 9), and the blender 31 mounted on the rotation mechanism rotates the inner part only via the blender rotation motor 32. Thus, the blade of the inner part (hereinafter referred to as the "internal blade") and the blade of the outer part (hereinafter referred to as "outer blade") are symmetrically rotated on the same axis, so that the inner blade and the outer blade are in contact with the tissue and cut the tissue.

The storage cooler 4 is disposed below the homogenizing sections 3. The storage cooler 4 holds and cools four sample containers 5. The sample container 5 contains tissue collected from a subject and buffer solution. Four openings 41 are provided at respective positions directly below the homogenizing sections 3 on the top surface of the storage cooler 4. The main body 10 has a brushless DC blade elevator motor 33 (refer to FIG. 9) to raise and lower the homogenizing sections 3 by driving the blade elevator motor 33. When the homogenizing sections 3 are lowered by the blade elevator motor 33, the blades 31 are inserted through the respective openings 41.

The sample containers 5 are arranged below the openings 41, and the blenders 31 are lowered through the holes 41 into the sample containers 5. The tip of the blender 31 is thus lowered to the bottom of the sample container 5, and the inner blade and outer blade are relatively rotated to homogenize the tissue in the sample container 5.

Figure 3:
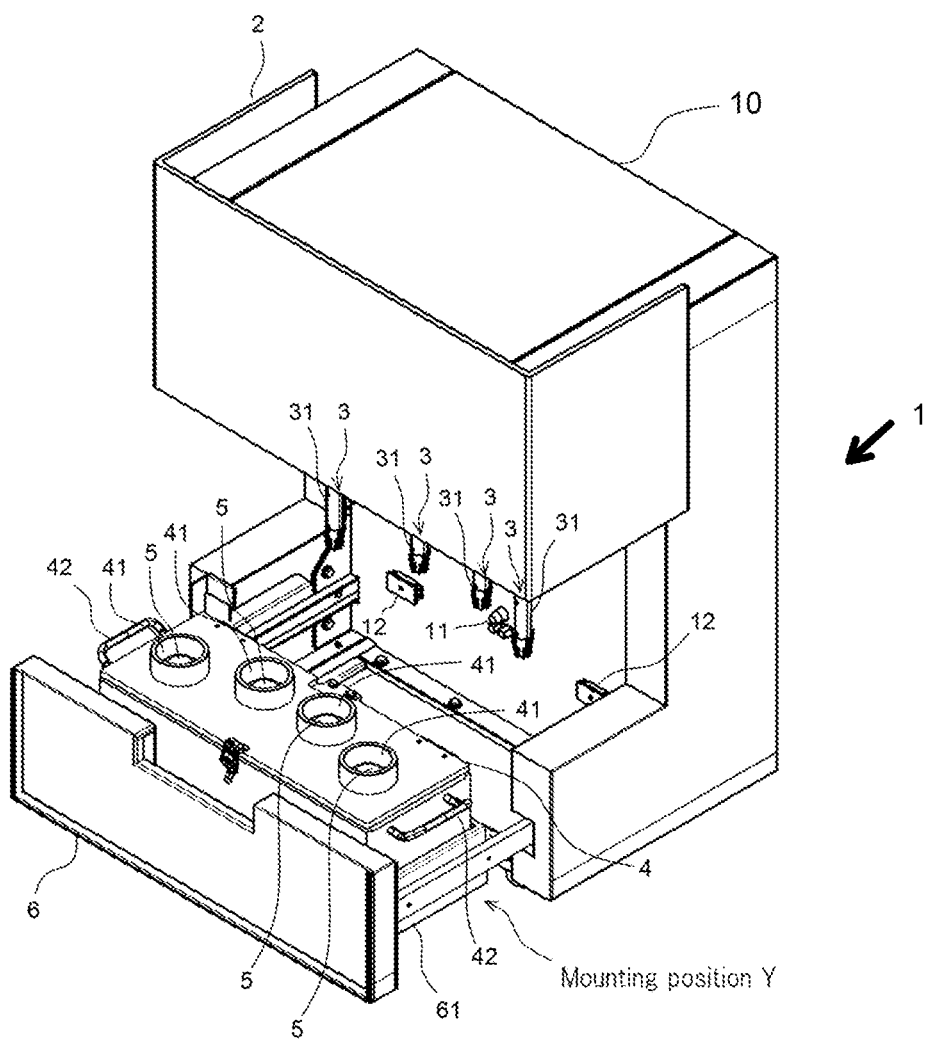
FIG. 3 is a perspective view showing the outer appearance of the homogenizer with the installation section pulled out.

The bottom section of the main body 10 is a drawer and can be pulled out toward the front. FIG. 3 is a perspective view showing the bottom section of the main body 10 pulled out from the main body. The bottom section of the main body 10 thus becomes an installation section 6 in which the operator sets the storage cooler 4. The installation section 6 is slidable forward and back along rails. That is, the installation section 6 is movable in the horizontal direction between the homogenizing positions X (position shown in FIG. 2) directly below the homogenizing sections 3, and the mounting position Y (position shown in FIG. 3) at which the storage cooler 4 is installed and removed.

Figure 4:
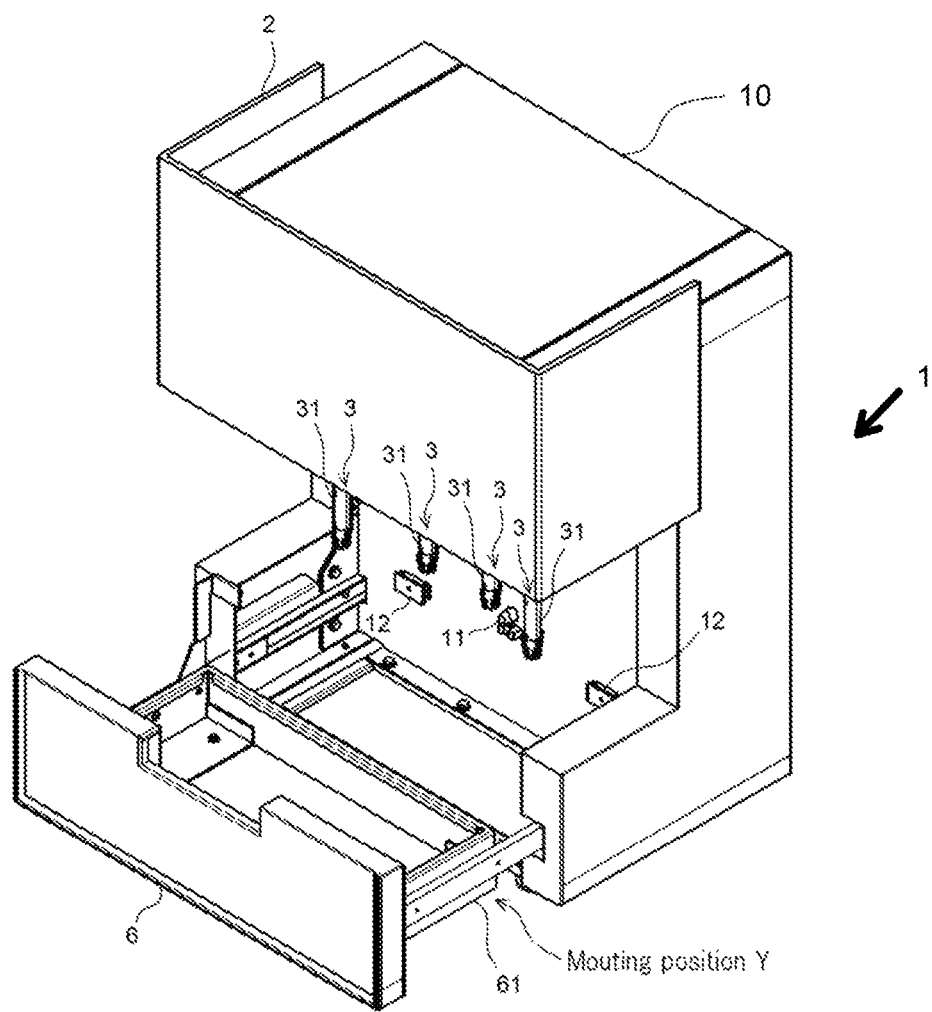
FIG. 4 is a perspective view showing the outer appearance of the homogenizer with the storage cooler removed.

When the installation section 6 is at the mounting position Y, the operator installs or removes the storage cooler 4 relative to the installation section 6. The storage cooler 4 is essentially a laterally elongated rectangular body with handles 42 provided at bilateral ends. FIG. 4 is a perspective view showing the homogenizer 1 with the storage cooler 4 removed. As shown in FIG. 4, the installation section 6 is provided with a receiver 61 for receiving the storage cooler 4. The receiver 61 is a dish-shaped square somewhat larger than the storage cooler 4, so that the storage cooler 4 can be accommodated on the receiver 61.

Figure 5:
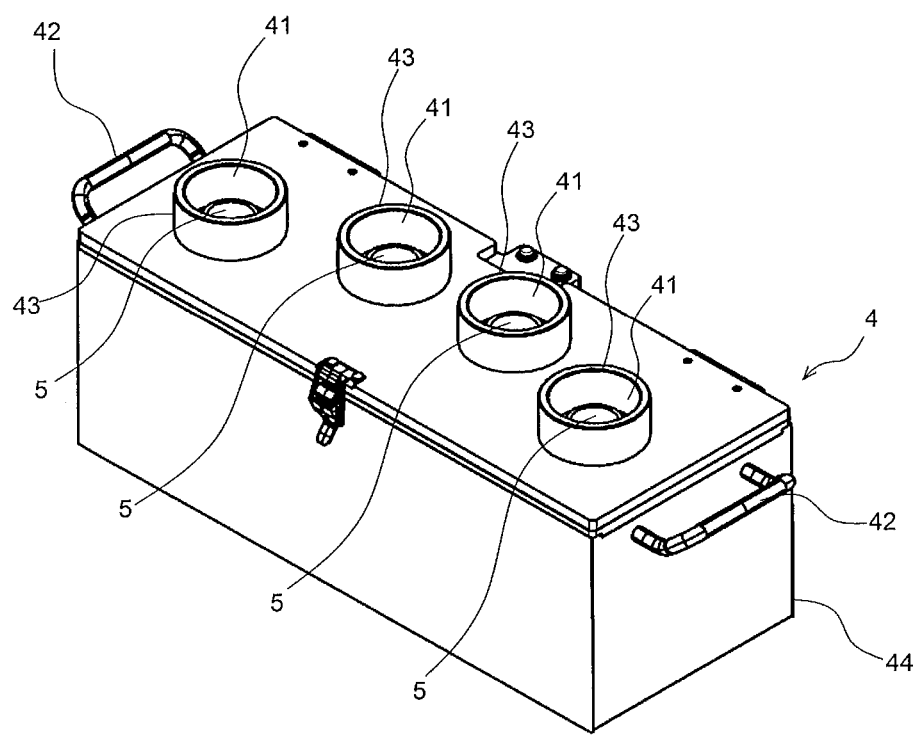
FIG. 5 is a perspective view showing the outward appearance of the storage cooler of the embodiment.

FIG. 5 is an exterior perspective view of the storage cooler 4. The storage cooler 4 is a rectangular cabinet. Four openings 41 are provided in the top surface of the storage cooler 4, and annular rings 43 extend from the rims of the openings 41. The rings 43 prevent airborne dispersion of tissue and buffer during the homogenizing process, and hence prevent contamination.

The two openings 41 on the outer side are arranged forward of the two openings 41 on the inner side. That is, the two inside openings 41 are arranged laterally parallel, and the rightmost opening 41 and the leftmost opening 41 are positioned forward of the two inside openings 41. Thus, since the positions of the two outside openings 41 and the positions of the two inside openings 41 are shifted in the front-to-back direction, the distance between the rightmost opening 41 and the adjacent opening 41, and the distance between the leftmost opening 41 and the adjacent opening 41 is longer to prevent contamination.

The top section of the storage cooler 4 is a cover 44a, which is hinged so as to open and close. A locking part 44b (see FIG. 6) is provided at the center of the front end of the cover 44a to secure cover 44a when closed.

Figure 6:
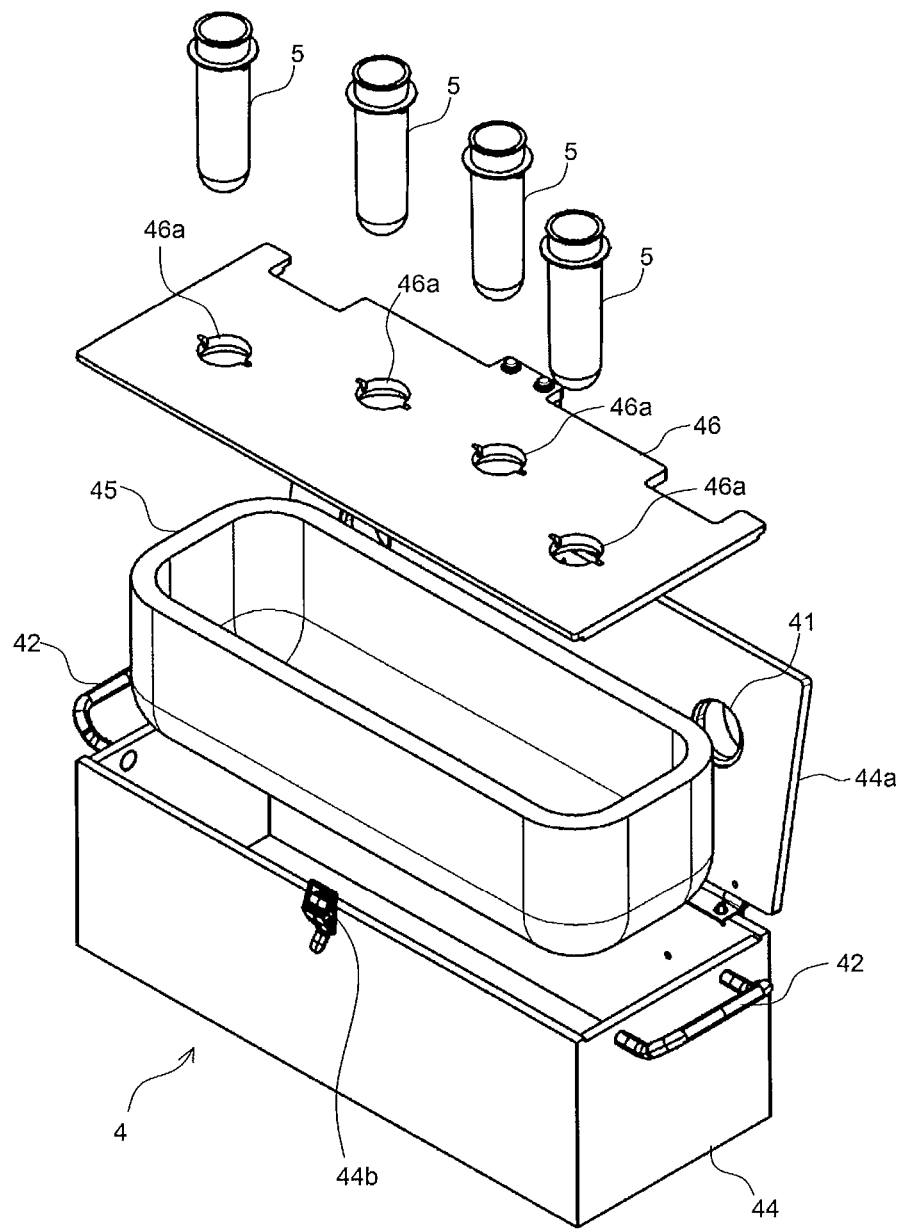
FIG. 6 is an exploded view showing the internal structure of the storage cooler.

FIG. 6 is an exploded perspective view showing the interior structure of the storage cooler 4. As shown in FIG. 6, the storage cooler 4 has a rectangular cabinet 44, cooling medium container 45 that holds a cooling medium, and inner cover 46 that holds the four sample containers 5. The top panel of the cabinet 44 is an outer cover 44a, and can be opened and closed as previously mentioned. The cooling medium container 45 and the inner cover 46 are housed inside the cabinet 44. The cooling medium container 45 is open at the top, and holds the cooling medium inside the container. The cooling medium is preferably ice, and ideally crushed ice (crushed ice with particles approximately 1 mm to 1 cm in diameter). Using crushed ice allows a larger surface area of contact between the cooling medium and the container side surfaces to obtain the greatest cooling efficiency. The opening at the top of the cooling medium container 45 is covered by the inner cover 46. The inner cover 46 has four holders 46a to hold the sample containers 5. The holders 46a are somewhat larger in diameter than the cylindrical tubes of the sample containers 5, and the inner cover 46 holds the sample containers 5 when the sample containers 5 are inserted into the holders 46a.

Figure 7:
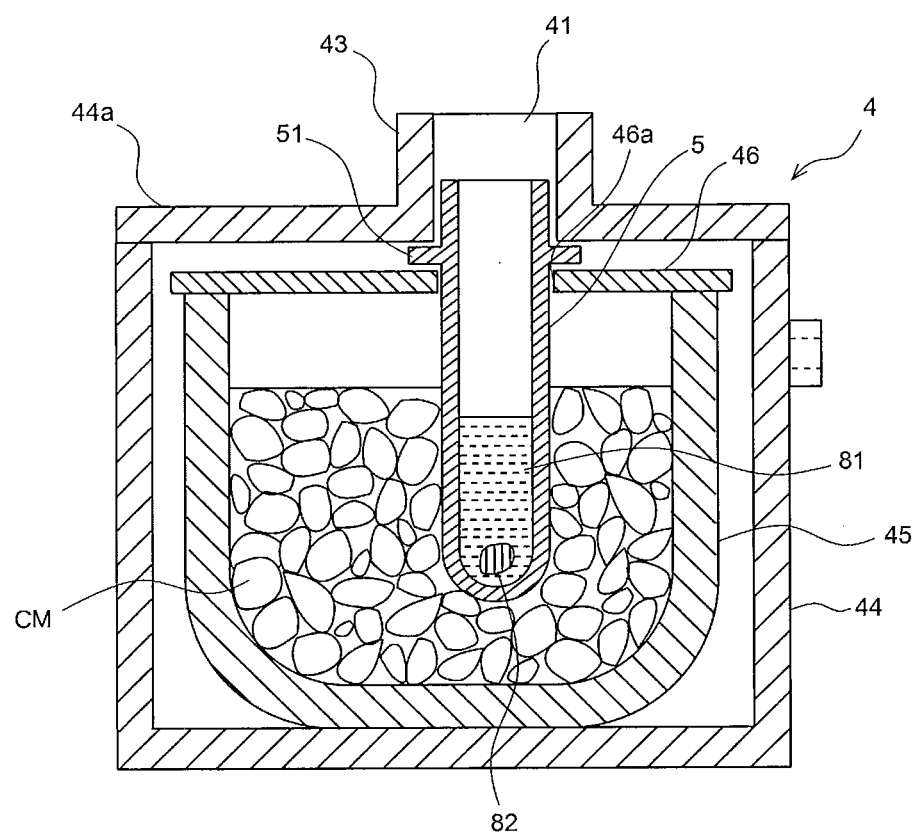
FIG. 7 is a cross sectional view of the storage cooler in the usable state.

FIG. 7 is a cross sectional view of the storage cooler 4 in the usable state. The sample container 5 is a tube like container made of plastic. The top end of the sample container 5 is open, and buffer 81 and tissue 82 are contained inside. A flange 51 which extends outward in an annular manner is provided at a position slightly below the top end of the sample container 5, and the outer diameter of the flange 51 is somewhat larger than the diameter of the holder 46a of the inner cover 46. Therefore, when the sample container 5 is inserted in the holder 46a, the sample container 5 is held in the holder 46a at a position abutting the flange 51.

The storage cooler 4 is used when the cover 44a is closed, crushed ice CM is accommodated in the cooling medium container 45, and sample containers 5 are held in the inner cover 46 in the cabinet 44. When the cover 44a is closed, the openings 41 and the holders 46a are aligned on the same axis. The top end of the sample container 5 is therefore inserted into the opening 41 when the cover 44a is closed. That is, the opening at the top end of the sample container 5 is exposed to the outside through the opening 41 provided in the cover 44a of the storage cooler 4, and the previously mentioned blender 31 therefore can be inserted inside the sample container 5 held in the storage cooler 4.

The outer diameter of the flange 51 of the sample container 5 is larger than the diameter of the opening 41 of the cover 44a. Therefore, when the sample container 5 is held in the inner cover 46 and the cover 44a is closed, the flange 51 is pressed by the part surrounding the opening 41 to prevent wobbling of the sample container 5 in the storage cooler 4.

The lower part of the sample container 5 held in the storage cooler 4 below the inner cover 46 is immersed in the crushed ice CM contained in the cooling medium container 45. Hence, the buffer and tissue within the sample container 5 are cooled. Note that the cooling medium is not limited to crushed ice, since other cooling media (dry ice, ice, gels, other coolant) also may be used insofar as the cooling medium is suitable for maintaining the storage temperature of the buffer being used. Preferable temperature of the buffer in the present embodiment is 2 to 8 degree Celsius. The temperature is preferably low enough to avoid degrading the cooling medium, but not freeze the cooling medium.

The storage cooler 4 can be removed from the main body 10 and used as a storage cooler outside the apparatus. For example, in a diagnosis of lymph node metastasis of cancer during a surgery, a tissue (lymph node) excised from the patient in a surgery is placed in a sample container 5 together with buffer. The sample container 5 is held in the storage cooler 4, and the tissue and buffer in the storage cooler 5 are cooled prior to the homogenizing process.

Figure 8:
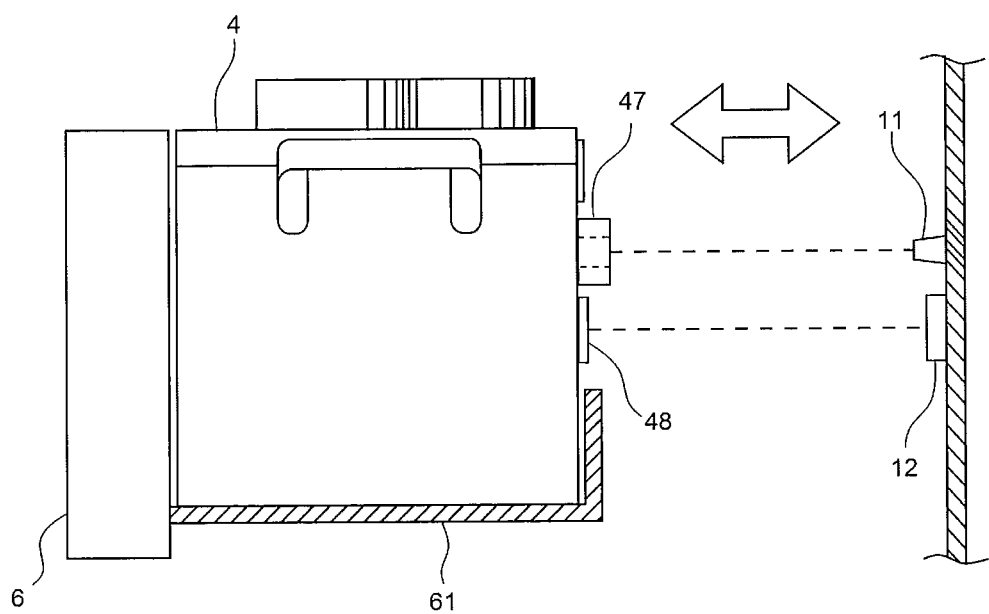
FIG. 8 is a side view schematically illustrating the movement of the installation section.

When performing the homogenizing process, the storage cooler 4 is mounted in the receiver 61 of the installation section 6 at the mounting position Y while holding the sample containers 5. Thereafter, the installation section 6 is slidably moved backward to the homogenizing position X. FIG. 8 is a side view schematically illustrating the movement of the installation section 6. As shown in FIG. 8, the back side of the storage cooler 4 has an annular hole 47 and a magnetic plate 48. As shown in FIGS. 3, 4, and 8, a positioning boss 11 and a magnet 12 are provided on the surface of the main body 10 that is opposite the storage cooler 4. The positioning boss 11 protrudes from the surface of the main body 10 opposite the storage cooler 4 at a position corresponding to the hole 47 of the storage cooler 4. The magnet 12 is provided on the surface of the main body 10 opposite the storage cooler 4 at a position corresponding to the magnetic plate 48 of the storage cooler 4. As shown in FIG. 8, when the installation section 6 accommodating the storage cooler 4 is moved backward from the mounting position Y, the positioning boss 11 is inserted into the hole 47 of the storage cooler 4 at the homogenizing position. Thus, the storage cooler 4 is aligned at the correct position (that is, the position at which the homogenizing section 3 can be inserted into the sample container 5) by inserting the positioning boss 11 into the hole 47 of the storage cooler 4. The storage cooler 4 is also anchored at the correct position when the magnet 12 magnetically attracts the magnetic plate 48 of the storage cooler 4. In this state, the homogenizing section 3 is inserted into the sample container 5 held in the storage cooler 4, and the homogenizing process is performed to pulverize the tissue.

Figure 9:
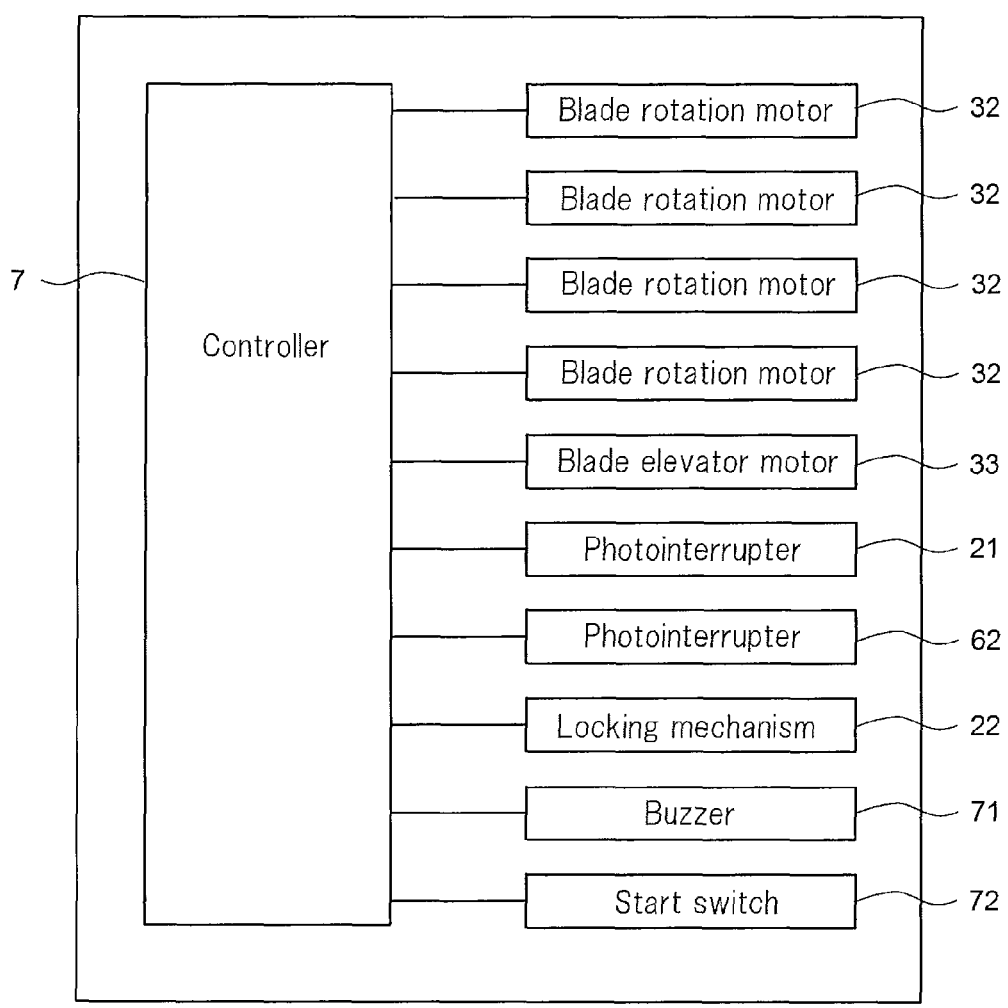
FIG. 9 is a block diagram showing the structure of the electrical circuit of the homogenizer of the embodiment.

FIG. 9 is a block diagram showing the structure of the electrical circuit of the homogenizer 1 of the embodiment. The main body 10 of the homogenizer 1 has a controller 7 configured by an FPGA (field-programmable gate array). The controller 7 is connected to the blade rotation motors 32 and blade elevator motor 33 so as to control the blade rotation motors 32 and blade elevator motor 33. A photointerrupter 21 configured to detect the closed cover 2 is provided in the housing of the main body 10. The photointerrupter 21 is connected to the controller 7 and outputs detection signals to the controller 7.

The main body 10 is also provided with a photointerrupter 62 configured to detect the storage cooler 4 installed in the installation section 6. More specifically, the photointerrupter 62 is disposed near the homogenizing position X so as to detect when the storage cooler 4 is installed in the installation section 6 at the homogenizing position X. Alternatively, the photointerrupter 62 does not detect the storage cooler 4 when the installation section 6 is not disposed at the homogenizing position X, or when the storage cooler is not installed in the installation section 6 at the homogenizing position X. The photointerrupter 62 is connected to the controller 7 and outputs detection signals to the controller 7.

The housing of the main body 10 is provided with a locking mechanism 22 configured to lock the cover 2 in the closed state. The locking mechanism 22 is connected to the controller 7 and controlled by the controller 7.

The housing of the main body 10 is provided with a buzzer 71, a start switch 72, status indicator 73 and emergency stop button 74. As shown in FIG. 1, the start switch 72 is a button switch provided on the front surface of the main body 10 and is operated by the operator. The buzzer 71, the start switch 72, the status indicator 73 and the emergency stop button 74 are connected to the controller 7, and the controller 7 controls the buzzer 71 and the status indicator 73, and receives the output signals from the start switch 72 and emergency stop button 74.

Operation of the Homogenizer

The method of use of the storage cooler 4 and the operation of the homogenizer 1 of the present embodiment are described below.

At the first, the cover 2 is opened by the operator and then the storage cooler 4 is removed from the main body 10. When the cover 2 is open, the operator pulls the installation section 6 forward from the homogenizing position X to the mounting position Y. The operator then removes the storage cooler 4 from the installation section 6 at the mounting position Y.

Then the operator opens the cover 44a and the inner cover 46 of the storage cooler 4, pours crushed ice into the cooling medium container 45, and covers the cooling medium container 45 with the inner cover 46. 4 mL of buffer is dispensed into the sample container 5 through the holder 46a of the inner cover 46 and the buffer is cooled. At most four sample containers 5 are prepared in this way. In this state, the arrival of tissue from the operating room is awaited.

When the tissue arrives, the operator introduces the tissue into the sample container 5 that contains the precooled buffer. The operator closes the outer cover 44a and secure the outer cover 44a with the cabinet 44 by the locking mechanism 44b in a state where the sample containers 5 are held on the inner cover 46.

With the cover 2 of the main body 10 in an open state, the operator attaches the blender 31 to the rotation mechanism of the homogenizing section 3. At most four blenders 31 are attached to homogenizing sections 3.

After the tissue has sufficiently cooled in the storage cooler 4 outside the main body 10, the operator installs the storage cooler 4 in the receiver 61 of the installation section 6 at the mounting position Y. The hole 47 of the storage cooler 4 faces backward. The operator slides the installation section 6 with the installed storage cooler 4 backward from the mounting position Y to the homogenizing position X. Thus, the positioning boss 11 is inserted into the hole 47 of the storage cooler 4, and the magnetic plate 48 is magnetically attached to the magnet 12. The installation of the storage cooler 4 in the main body 10 is therefore completed.

Figure 10:
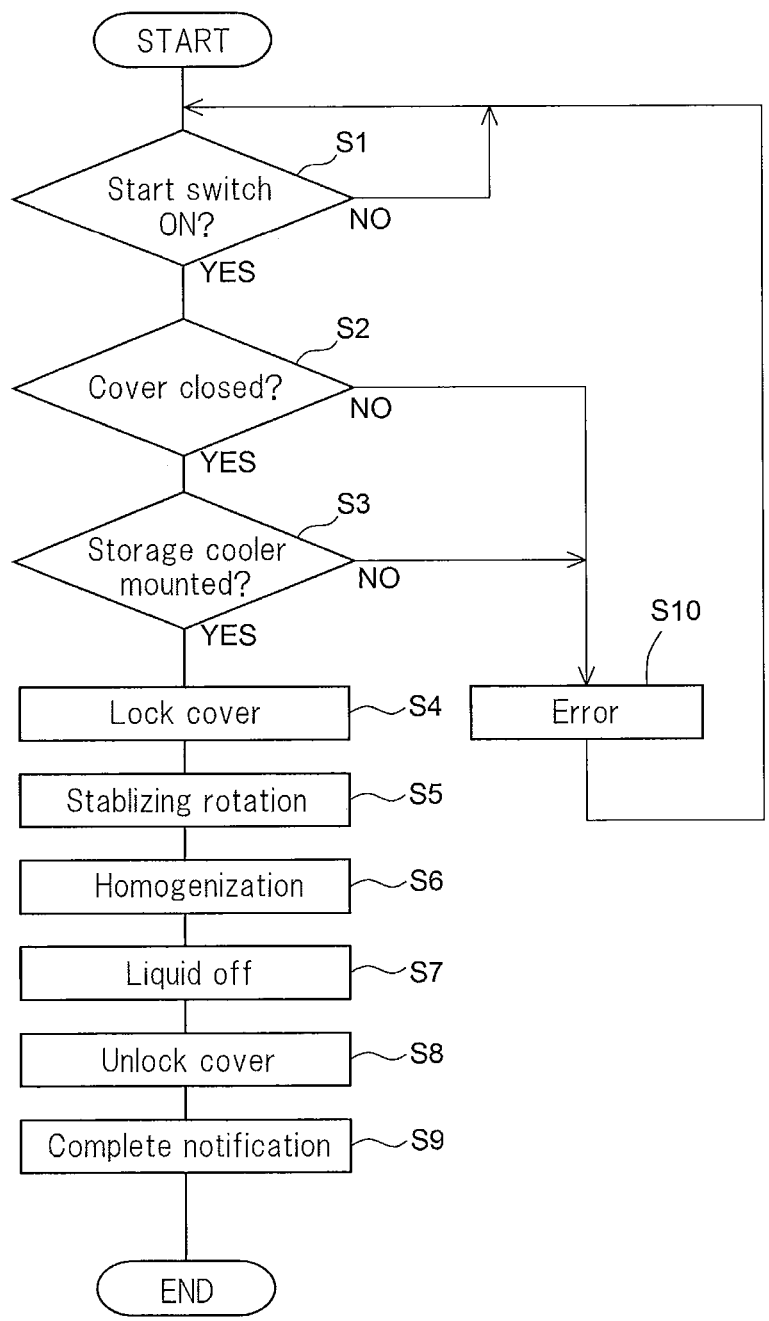
FIG. 10 is a flow chart showing the flow of the operation of the embodiment of the homogenizer.

The operation of the homogenizer 1 is described below with a reference of FIG. 10. FIG. 10 is a flow chart showing the operating sequence of the embodiment of the homogenizer 1. The operator closes the cover 2 and presses the start switch 72 to issue an instruction to execute the tissue homogenizing process in the homogenizer 1. The controller 7 is awaiting the instruction to start the homogenizing process. If the start switch 72 is pressed, that is, the controller 7 receives the instruction to start (step S1: YES), operation proceed to the step S2. If the start switch 72 is not pressed, the controller 7 repeats the determination of step S1.

The controller 7 detects whether the cover 2 is closed (step S2). The determination whether the cover 2 is closed or not is made with reference to the output signal from the photointerrupter 21. If the cover 2 is not closed (step S2: NO), the controller 7 issues an error in the step S10, in order to notify the operator that the cover 2 is not closed. In the error process (step S10), the buzzer 71 sounds and the status indicator 73 flashes with red, the color indicates an error occurs. Error operation is terminated after a predetermined time elapsed, and the operation returns to the step S1.

When the closed cover 2 is detects in step S2 (step S2: YES), the controller 7 determines whether the storage cooler 4 is installed (step S3). When the storage cooler 4 is installed in the installation section 6 and the installation section 6 is moved to the homogenizing position X as described above, the photointerrupter 21 detects the storage cooler 4 and outputs a corresponding detection signal. The controller 7 detects the installed storage cooler 4 in the main body 10 by receiving the detection signal. When the storage cooler 4 is not detected in step S3 (step S3: NO), the controller 7 issues the error in the step S10, in order to notify the operator that the storage cooler 4 is not installed.

When the storage cooler 4 installed in the main body 10 is detected in step S3 (step S3: YES), the controller 7 controls the locking mechanism 22 to lock the cover 2 (step S4). Thus, the operator mistakenly touching the homogenizing sections 3 is prevented.

Figure 11:
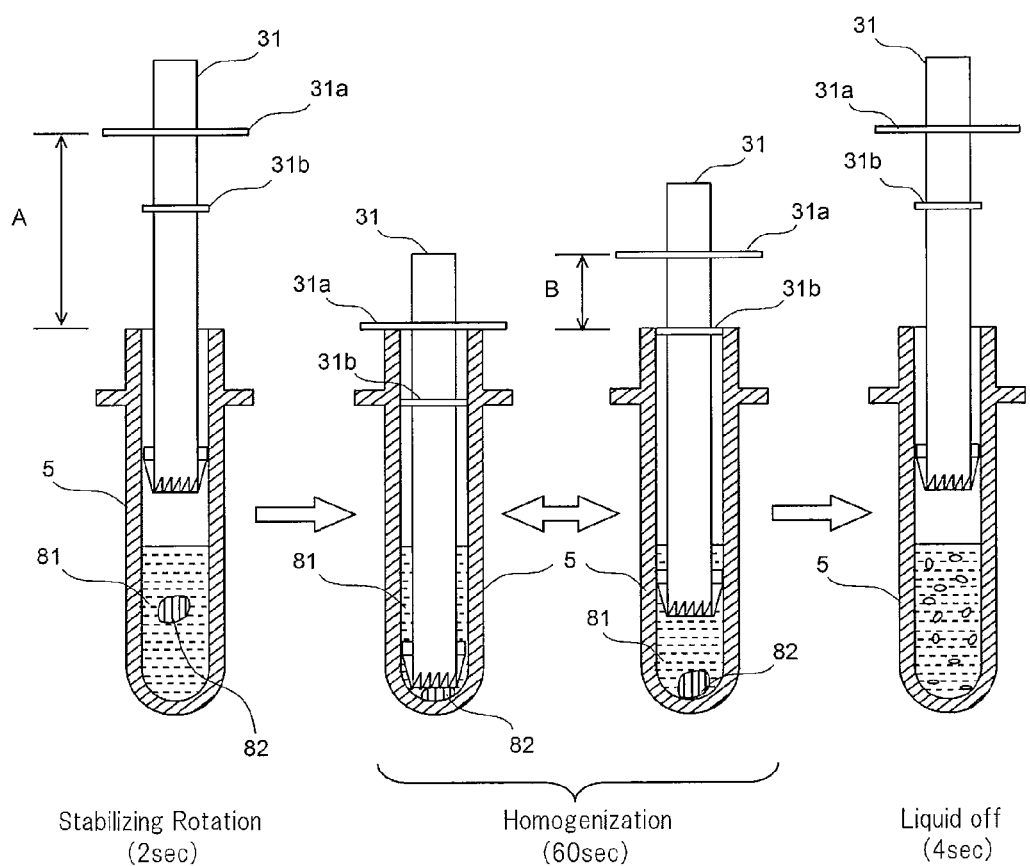
FIG. 11 is a schematic view illustrating the operation of the homogenizing section.

The controller 7 then controls the blade rotating motors 32 and the blade elevator motor 33 to execute the rotation stabilizing operation (step S5). FIG. 11 is a schematic view illustrating the operation of the homogenizing section 3. The blender 31 is provided with an annular flange 31a that protrudes outwardly. The external diameter of the flange 31a is greater than the external diameter of the opening of the sample container 5. In the rotation stabilizing operation, the homogenizing section 3 is lowered and the flange 31a on the blender 31 is positioned a distance A from the top end of the sample container 5, and the inner blade of the blender 31 is rotated. Leading end of the blender 31 is positioned near the center in the longitudinal direction of the sample container 5, above the liquid surface of the buffer 81. The rotation stabilizing operation is performed for 2 seconds. The rotation of the homogenizing section 3 is thus performed stably.

The controller 7 then controls the blade rotating motors 32 and the blade elevator motor 33 to execute the homogenizing operation (step S6). As shown in FIG. 11, the homogenizing operation is accomplished by the relative rotation of the inner blade and outer blade of the blender 31 while alternatively lowering and raising the blender 31 in the sample container 5. In the homogenizing operation, the blender 31 reciprocates between a first position at which the tip of the blender 31 is near the bottom of the sample container 5 and a second position at which the tip of the blender 31 is a predetermined distance B above the first position. More specifically the second position is higher than the bottom of the sample container 5 and lower than the liquid level of the buffer 81.

Since the tip of the blender 31 is disposed near the bottom of the sample container 5 at the first position, the inner blade and the outer blade of the blender 31 are in contact with the tissue and the tissue is crushed and homogenized by the relative rotations of the inner blade and the outer blade. The flange 31a of the blender 31 abuts the top end of the sample container 5 at the first position. That is, the flange 31a closes the opening of the sample container 5 to prevent airborne dispersion of the mixture of tissue and buffer from the sample container 5 by the rotational operation of the blender 31.

The tip of the blender 31 is above the bottom of the sample container 5 at the second position so as to be disposed beneath the surface level of the buffer. Therefore, the pulverized tissue particles and buffer are mixed and the clogging of the inner blade and the pouter blade by tissue is prevented. An annular flange 31b is provided on the blender 31 below the flange 31a. The outer diameter of the flange 31b is slightly smaller than the inner diameter of the sample container 5. When the blender 31 is at the second position, the flange 31b is positioned at the top end of the sample container 5. That is, the flange 31b closes the opening of the sample container 5 to prevent airborne dispersion of the mixture of tissue and buffer from the sample container 5 by the rotational operation of the blender 31.

Figure 12:
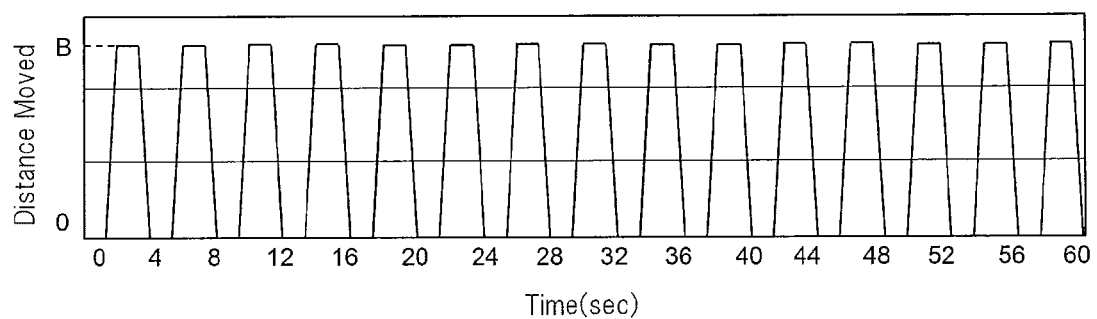
FIG. 12 is a graph showing the relationship between time and the moving distance of the homogenizing section during the homogenizing operation.

FIG. 12 is a graph illustrating the raising and lowering of the homogenizing section 3 in the homogenizing operation. In the drawing, the vertical axis represents the position of the blender 31 and the horizontal axis represents the time. Also in the drawing, the blender 31 is stopped for approximately 1 second at the lowermost first position, and thereafter raised from the first position a distance B to the second position. The blender 31 is also stopped for approximately 1 second at the uppermost second position, and thereafter lowered to the first position. The raising and lowering of the homogenizing section 3 is repeated many times during the homogenizing operation. During this time the inner blade of the blender 31 is continuously rotated. The homogenizing operation is performed for 60 seconds.

In the homogenizing operation, the inner blade and the outer blade within the blender 31 efficiently stir the mixture of tissue and buffer without remaining at a fixed position because the blender 31 performs the rotation operation while moving reciprocatingly between the first position and the second position. The tissue particles are prevented from remaining adhered to the inner wall of the sample container 5 and the homogenized tissue particles are of uniform size.

When the homogenizing operation ends, the controller 7 controls the blade rotation motors 32 and the elevator motor 33 to perform a liquid off operation (step S7). In the liquid off operation, the homogenizing section 3 is raised and the flange 31a on the blender 31 is disposed at a position (the same position as the rotation stabilizing operation) a distance A above the top end of the sample container 5 while the inner blade and the outer blade of the blender 31 are rotated. Leading end of the blender 31 is positioned near the center in the longitudinal direction of the sample container 5, above the liquid surface of the buffer. Therefore, the tissue particles and buffer adhered to the inner blade and the outer blade are removed from the blender 31, and airborne dispersion of the tissue particles and buffer is prevented outside the sample container 5. The liquid cutting operation is performed for 4 seconds.

When the liquid off operation is completed, the controller 7 controls the locking mechanism 22 to unlock the cover 2 (step S8). The controller 7 also operates the buzzer 71 to alert the operator that homogenizing has ended (step S9) and the operation ends. Note that the controller 7 interrupts the homogenizing operation, raises the homogenizing section 3 and unlock the cover 2 when the emergency stop button 74 is pressed during the homogenizing operation of step S6.

The operator opens the cover 2 and pulls the installation section 6 forward from the homogenizing position X to the mounting position Y. The operator then removes the storage cooler 4 from the installation section 6 at the mounting position Y. The operator confirms whether homogenization has been sufficiently performed in the sample container 5. The operator also confirms whether tissue particles remain on the end of the blender 31. When there has been insufficient homogenization or the tissue particles remain adhered to the sample container 5 or the blender 31, the operator installs the storage container 4 directly in the main body 10 and re-performs the homogenizing operation.

When sufficient homogenization is confirmed, the operator caps the sample container 5, removes the capped sample container 5 from the storage cooler 4, and sends the sample container 5 for genetic testing. The operator also removes the blender 31 from the main body 10 and disposes of the blender 31.

According to the present embodiment of the homogenizer 1 as described in detail above, the operator removes the storage cooler 4 from the main body 10 and cools the sample containers 5 containing the tissue in the storage cooler 5 before performing the homogenizing operation. When the preprocessing is performed, the storage cooler holding the precooled sample containers 5 is installed directly in the main body. Therefore, the container for cooling the sample container before performing preprocessing, and the cooler for cooling the sample container while homogenization is performed are both combined in the storage cooler 4.

Since the installation section 6 is configured to be slidable between the homogenizing position X and the mounting position Y, the storage cooler 4 can be easily installed in the main body 10 by installing the storage cooler in the installation section 6 at the mounting position Y then moving the installation section 6 to the homogenizing position X. When the storage cooler 4 is loaded in the main body 10, the storage cooler 4 can be easily removed from the main body 10 by moving the installing section 6 from the homogenizing position X to the installing position Y and extracting the storage cooler 4 from the installation section 6.

When the storage cooler 4 is not installed in the main body 10, the absence of the storage cooler 4 is detected by the photointerrupter 62 and the homogenizing operation is not performed. Damage to the apparatus due to unexpectedly performing homogenizing operation when tissue is not present to be homogenized can therefore be prevented. When the storage cooler 4 is installed in the main body 10, the presence of the storage cooler 4 is also detected by the photointerrupter 62 and the homogenizing operation is performed when the start switch 72 is turned ON and detected. Therefore, the tissue in the sample container held in the storage cooler 4 can be homogenized insofar as the storage cooler 4 is installed.

In addition to the installation of the storage cooler 4, when the cover 2 is closed, the closed cover 2 is detected by the photointerrupter 21 and the homogenizing operation is performed when the start switch 72 is turned ON and detected. Therefore, the inside and outside of the main body 10 are blocked by the cover 2 during the homogenizing operation, so that the operator is prevented from touching the inside of the main body 10 and airborne dispersion of tissue and buffer outside the homogenizer 1 by the homogenizing operation is also prevented. Although there is a possibility that the operator might touch the inside of the apparatus when the cover 2 is not closed, the open cover 2 is detected by the photointerrupter 21 and the homogenizing operation is not performed even though the start switch 72 is turned ON.

If the start switch 72 is turned ON and detected when the storage cooler 4 is installed and the cover 2 is closed, the cover 2 is locked and the homogenizing operation is performed. Therefore, the cover 2 is prevented from opening during the homogenizing operation.

Since the homogenizing section 3 performs the liquid cutting operation after the homogenizing operation, the tissue adhered to the homogenizing section 3 by the homogenizing operation is removed and contamination is prevented.

Since the storage cooler 4 can hold four sample containers 5, the storage cooler 4 can cool a maximum of four sample containers 5 simultaneously. Also preprocessing of a plurality of tissues can be accomplished efficiently since the homogenizer 1 is configured to homogenize tissue simultaneously in a maximum of four sample containers 5.

When homogenizing the tissue in the sample container 5 held in the storage cooler 4, the tissue in the sample container 5 is cooled and directly homogenized since the homogenizing section 3 is inserted into the storage cooler 4 through the opening 41 and homogenizes the tissue in the sample container 5.

Second Embodiment

Homogenizer Structure

Figure 13:
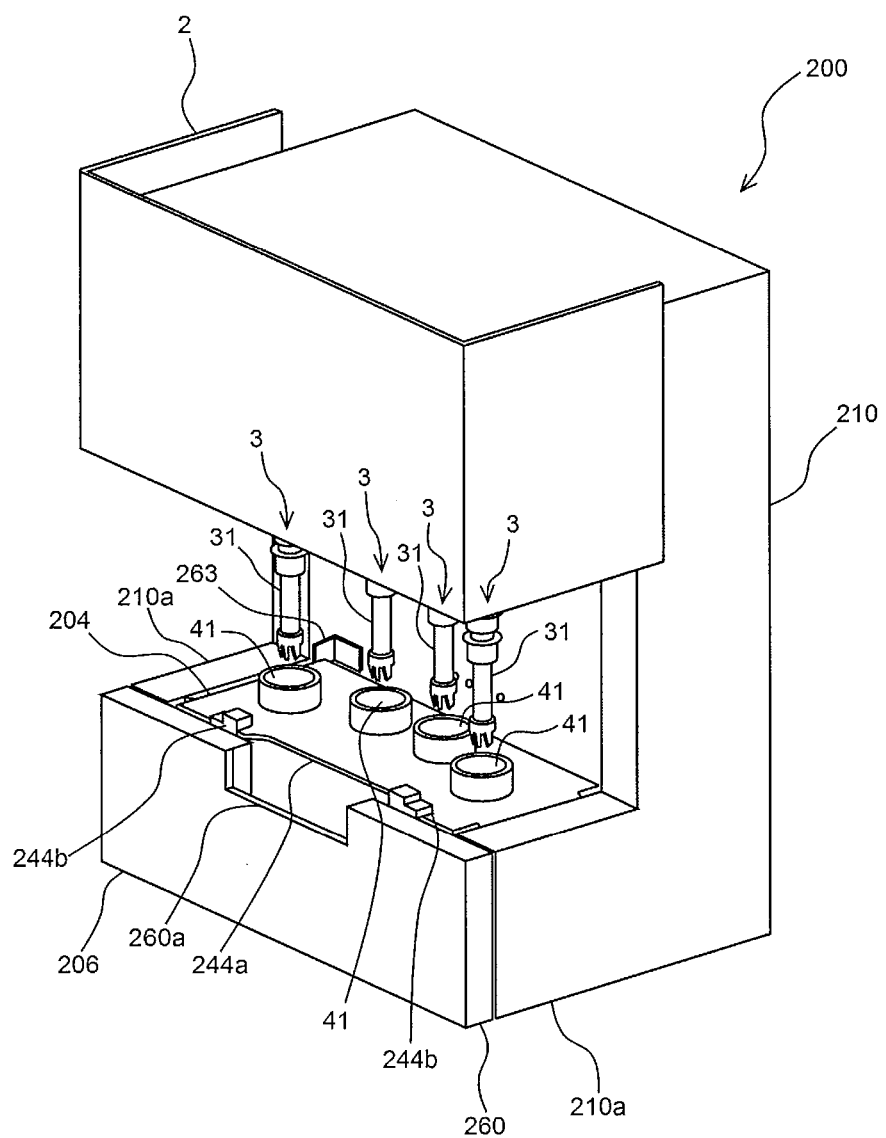
FIG. 13 is a perspective view showing the outward appearance of a second embodiment of the homogenizer.

FIG. 13 is a perspective view showing the outward appearance of an embodiment of the homogenizer. The homogenizer 200 of the present embodiment is similar to the homogenizer 1 of the first embodiment inasmuch as it is an apparatus installed in a laboratory in a hospital, which is for mainly for homogenizing tissue in a buffer solution, the tissue being collected from a patient during surgery. The homogenizer 200 is provided with an essentially rectangular main body 210, and storage cooler 204 that is removable from the main body 210. The main body 210 is provided with a cover 2 that covers part of the front surface. The cover 2 is configured to slide vertically so as to open and close. FIG. 13 shows the cover 2 in the closed state.

Note that structural aspects of the homogenizer 200 of the present embodiment which are identical to structural aspects of the homogenizer 1 of the first embodiment are denoted by similar reference numbers.

Figure 14:
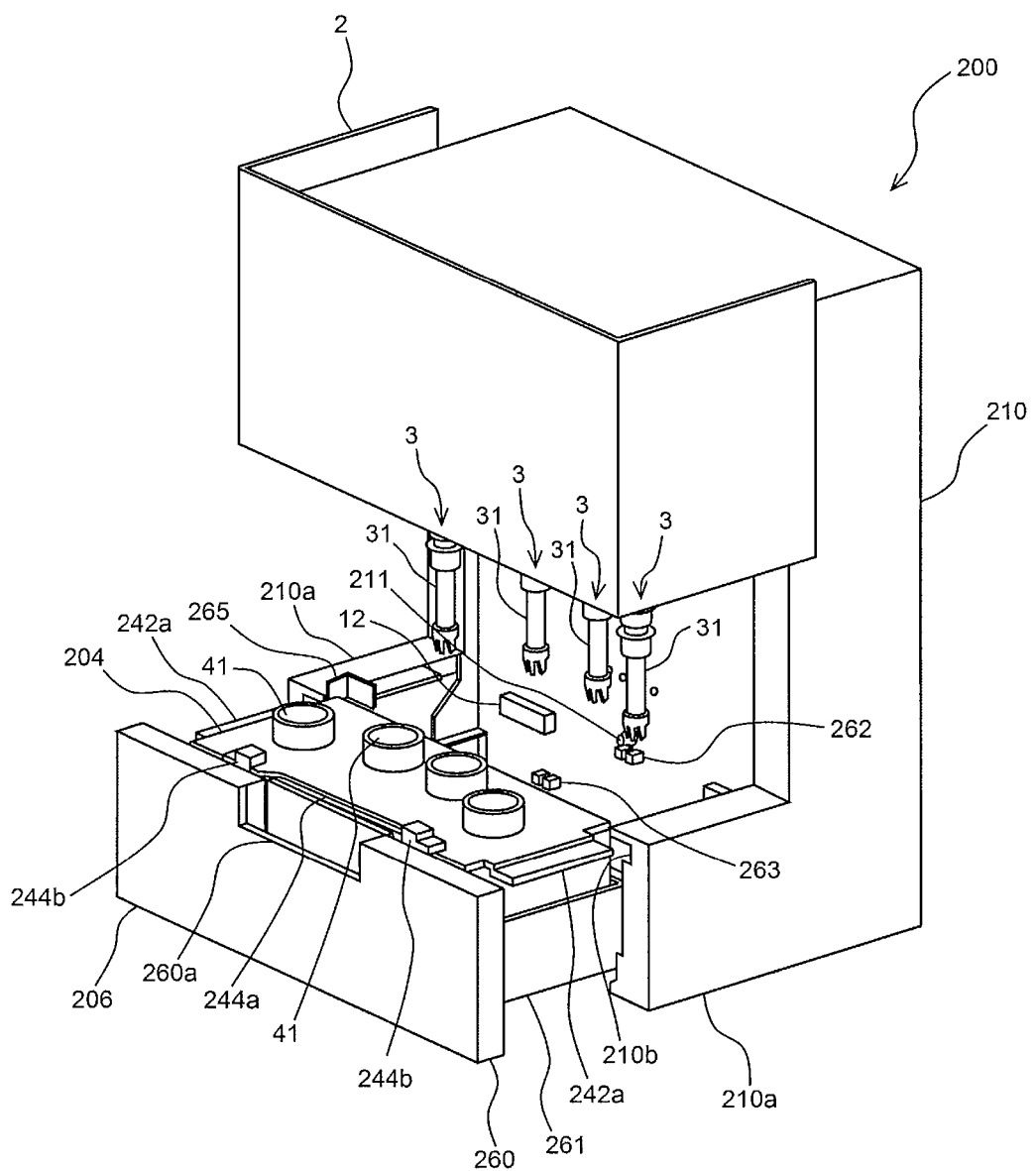
FIG. 14 is a perspective view showing the outward appearance of the homogenizer with the installation section pulled out.

An installation section 206, which is slidable in horizontal directions, is provided at the bottom part of the main body 210. The storage cooler 204 is installed in the installation section 206. FIG. 14 is a perspective view showing the homogenizer 200 with the installation section 206 pulled out. The installation section 6 is movable in the horizontal direction between the homogenizing position X (position shown in FIG. 13) directly below the homogenizing sections 3, and the mounting position Y (position shown in FIG. 14) at which the storage cooler 204 is installed and removed. The installation section 206 has a receiver 261 for receiving the storage cooler 204. The receiver 261 is a dish-shaped square somewhat larger than the bottom of the storage cooler 204, so that the storage cooler 204 can be accommodated on the receiver 261.

Figure 15:
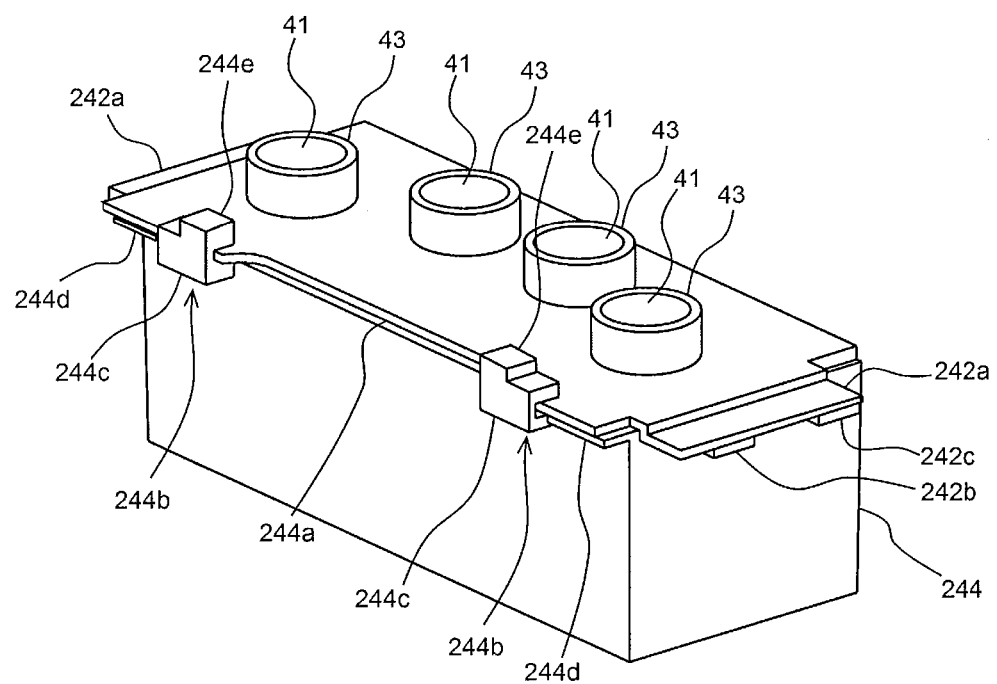
FIG. 15 is a perspective view showing the outward appearance of the storage cooler of the second embodiment.
Figure 16:
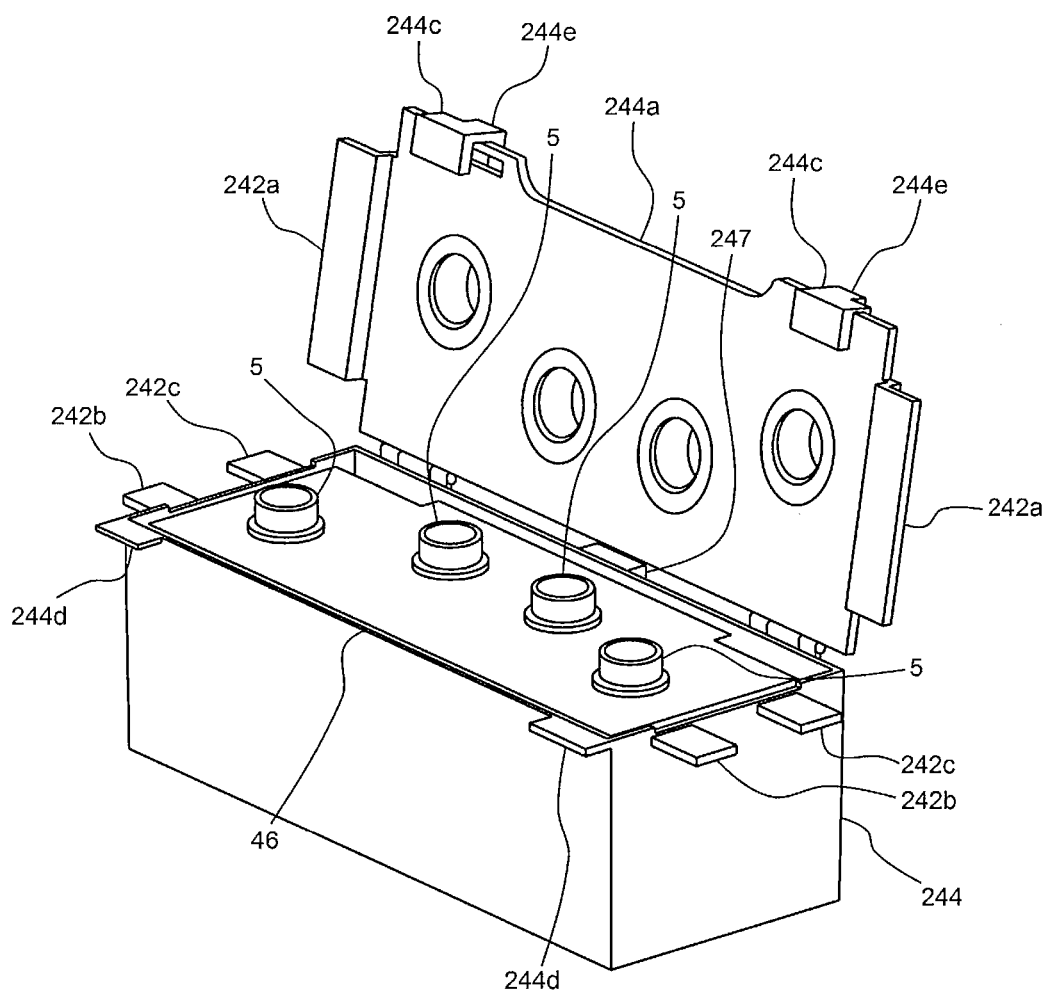
FIG. 16 is a perspective view showing the outward appearance of the storage cooler of the second embodiment with cover opened.

FIGS. 15 and 16 are perspective views showing the exterior appearance of the storage cooler 204. The storage cooler 204 is a rectangular cabinet. The top section of the storage cooler 204 is a cover 244a, which is hinged so as to open and close. Locking parts 244b of the cover 244 are provided at two places on the front edge of the storage cooler 204 to secure the cover 244a when closed.

The locking parts 244b are configured by operating parts 244c mounted on the cover 244a, and engaging projections 244d which are provided on the front edge of the main body cabinet 244 of the storage cooler 204. The engaging projections 244d are flat shaped, and respectively project forward from the bilateral ends of the front edge of the top opening of the cabinet 244. The operating parts 244c are provided on the front edge of the cover 244a so as to be laterally slidable. The operating parts 244c are respectively laterally slidable within a predetermined range; the position of closest mutual proximity being the release position, and the position of greatest mutual separation being the lock position. That is, when the cover 244a is closed and the operating parts 244c are slid so as to move away from the release position, the engaging projections 244d are clipped by the operating parts 244c together with parts of the outer cover 43 thereby the cover 244a is locked. When the operating parts 244c are slid so as to mutually approach from the lock position, the engagement is released between the operating parts 244c and the engaging projections 244d so as to unlock the cover 244a.

The operating parts 244c are provided with knobs 244e which project upward. Since the knobs 244e project upward, the operator can easily grasp the knobs 244e to operate the operating parts 244c.

Flat shaped projections 242a are provided at the both sides of the cover 244a. A pair of flat shaped projections 242b and 242c are also provided from one side of the cabinet 244, and another pair of flat shaped projections 242b and 242c are similarly provided from the other side of the cabinet 244. When the cover 244a is closed, the pair of projections 244b and 244c of the cabinet 244 overlap the projection 242a of the cover 244a so as to function as a single handle. That is, a pair of handles are provided on both lateral sides of the storage cooler 204.

Figure 17:
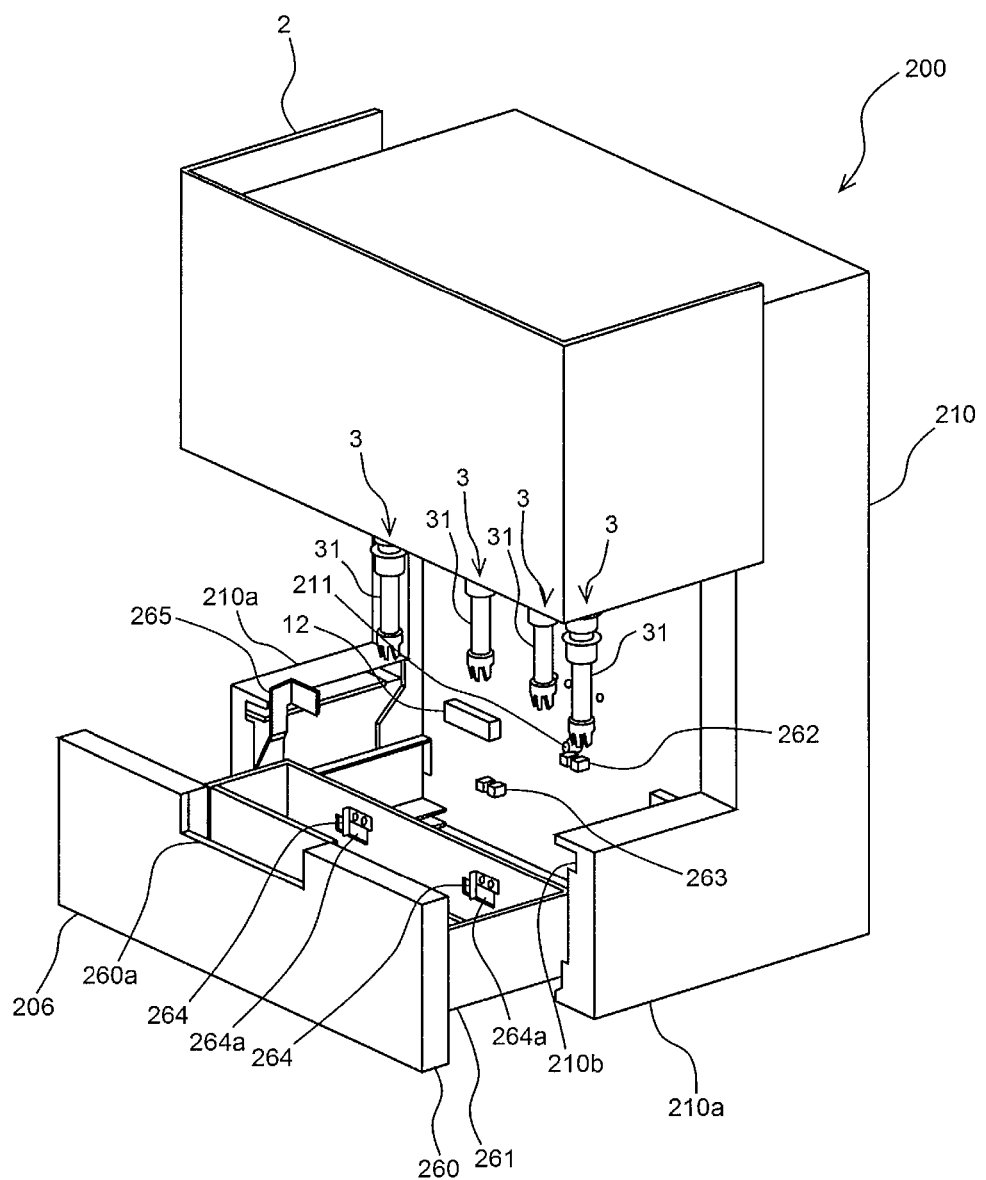
FIG. 17 is a perspective view showing the outward appearance of the homogenizer with storage cooler removed.

When the installation section 206 is at the mounting position Y, the operator installs the storage cooler 204 in the installation section 206 or removes the storage cooler 204 from the installation section 206 (refer to FIG. 13). FIG. 17 is a perspective view showing the homogenizer 200 with the storage cooler 204 removed. As shown in FIG. 17, the storage cooler 204 is installed on the receiver 261 provided in the installation section 206.

The operator grasps the handles of the storage cooler 204, and then mounts or removes the storage cooler 204 in/from the installation section 206. When the projecting parts 242a, 242b, 242c are used as handles in this manner, the operator can place her/his fingers above and below to grip the overlaid projecting parts 242a, 242b, 242c therebetween. The projecting parts 242a of the cover 244a also function as handles for closing and opening the cover 244a. That is, the pair of projecting parts 242b and 242c of the cabinet 244 are mutually separated with a gap therebetween, as shown in FIGS. 15 and 16. If a finger is inserted between the pair of projecting parts 242b and 242c, therefore, the operator can grasp only the projecting part 242a of the cover 244. The operator can thus open and close the cover 244a by lifting and lowering while grasping the projecting parts 242a of both sides.

Figure 18:
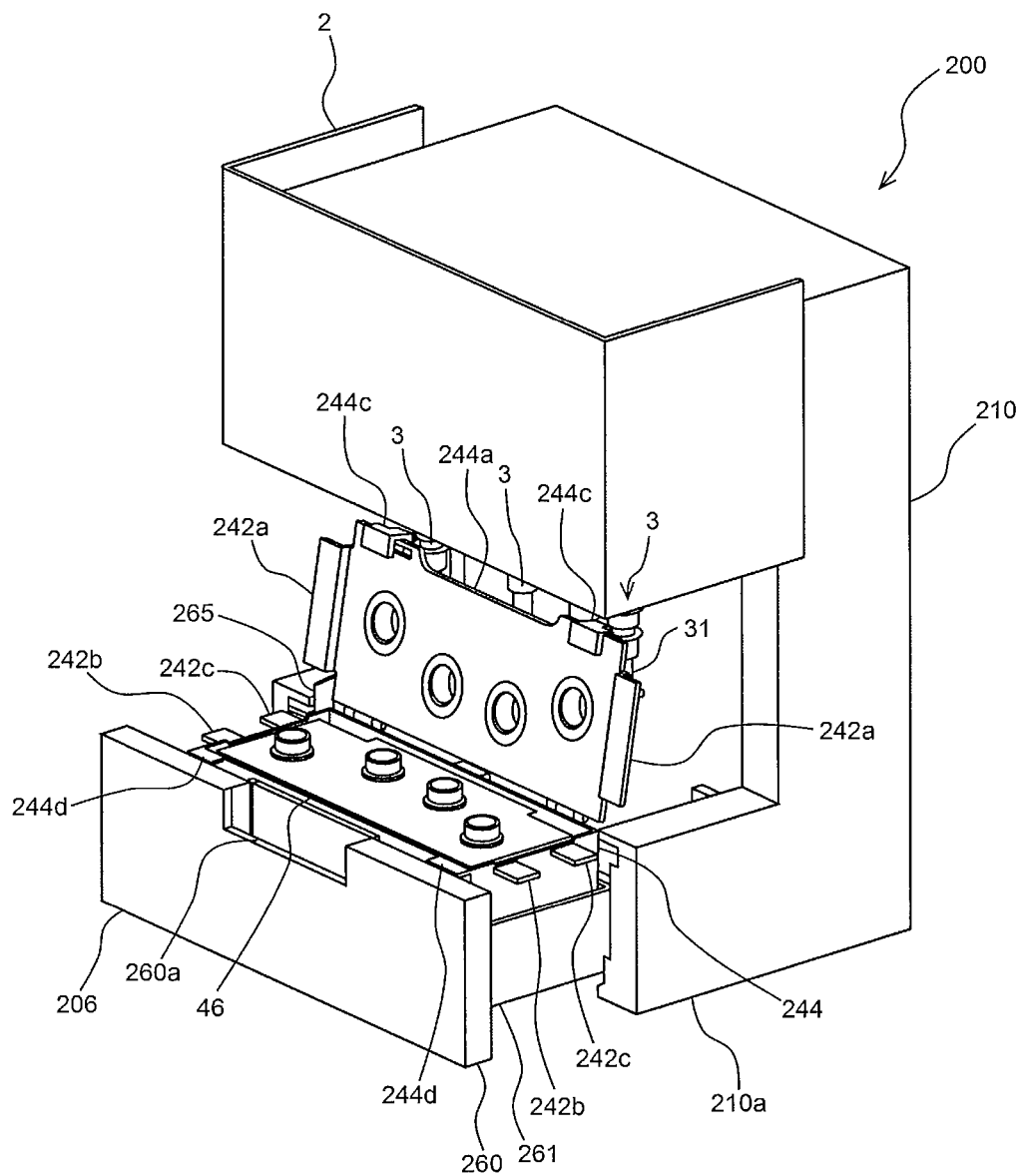
FIG. 18 is a perspective view showing the outward appearance of the homogenizer with the installation section pulled out and cover of storage cooler opened.

The cover 244a can be opened and closed both when the storage cooler 204 is removed from the main body 210, and when the storage cooler 204 is installed in the installation section 206 at the mounting position Y. FIG. 18 is a perspective view showing the homogenizer 200 when the cover 244a is open and the storage cooler 204 is mounted. When the installation section 206 is disposed the mounting position Y as shown in FIG. 18, the operator can open and close the cover 244a of the storage cooler 204. The sample containers can be quickly retrieved from the storage cooler 204 after the homogenizing process, or the next unprocessed sample containers can be quickly installed in the storage cooler 204.

A contact member 265 is provided on the installation section 206 as shown in FIG. 17. The contact member 265 is plate shaped and disposed so as to extend upward from the side part of the receiver 261, the top part of the member being bent 90 degrees so that the surface is parallel to the back surface of the receiver 261. This surface is positioned above the back surface of the receiver 261 so as to contact the cover 244a when the cover 244a of the storage cooler 204 is opened, hence functioning as a stopper to prevent the cover 244a from opening too far.

When the installation section 206 is disposed at the mounting position Y and the cover 244a of the storage cooler 204 seated on the receiver 261 is open, as shown in FIG. 18, the cover 244a is tilted to be more than 90 degrees and comes into contact with the contact member 265. Opened cover is maintained in such angle. The cover 244a does not interfere with the blenders 31 at this position. Hence, contamination is prevented by preventing tissue and buffer from adhering to the cover 244a through contact with the blenders 31.

As shown in FIG. 14, the front part of the installation section 206 is plate-like part 260 that is flat in the vertical length, and a concave handhold 260a is provided at the center top edge of the plate-like part 260. When moving the installation section 206 between the mounting position Y and the homogenizing position X, the operator grips the handhold 260a and pulls the installation section 206 from the main body 210 and pushes the installation section 206 into the main body 210.

The bilateral parts of the housing bottom of the main body 210 are guides 210a, which extend forward so that the installation section 206 is arranged between the two guides 210a when the installation section 206 is at the homogenizing position X. The front edge surfaces of the guides 210a face the bilateral back surface of the plate-like part 260 of the installation section 206. The front edge surface of the guides 210a are partially eliminated so as to form notches 210b. When the cover 244a is closed and the storage cooler 204 is loaded in the installation section 206 and the installation section 206 is moved backward from the mounting position Y, the projecting parts 242a, 242b, 242c do not interfere with the front edge surface of the guides 210a due to the notches 210b, such that the installation section 206 can be moved to the homogenizing position X.

When the installation section 206 loaded with the storage cooler 204 is at the homogenizing position X as shown in FIG. 13, the projecting parts 242a, 242b, 242c of the storage cooler 204 are housed on the inner side the guides 210a. That is, the top surfaces of the guides 210a are positioned above the projecting part 242a. The cover 244a of the storage cooler 204 is thus prevented from opening at the homogenizing position X. Damage or accidents caused by opening of the cover 244a of the storage cooler 204 are thus prevented during the homogenizing process.

As shown in FIG. 17, a positioning boss 211 and a magnet 12 are provided on the surface of the main body 210 that is opposite the storage cooler 204. The positioning boss 211 is a projection provided on the surface facing the storage cooler 204. A photointerrupter 262 which detects the storage cooler 204 is provided below the positioning boss 211. A photointerrupter 263 which detects the installation section 206 is provided at two locations laterally separated from the center of the main body below the photointerrupter 262 (only one of the two photointerrupters 263 is shown in FIG. 17).

As shown in FIG. 17, holes 264a are respectively provided at two separate locations on the right and left of the back surface panel of the installation section 206, and detection pieces 264 which are plate shaped with a vertical length are respectively provided forward of the holes 264a.

Figure 19:
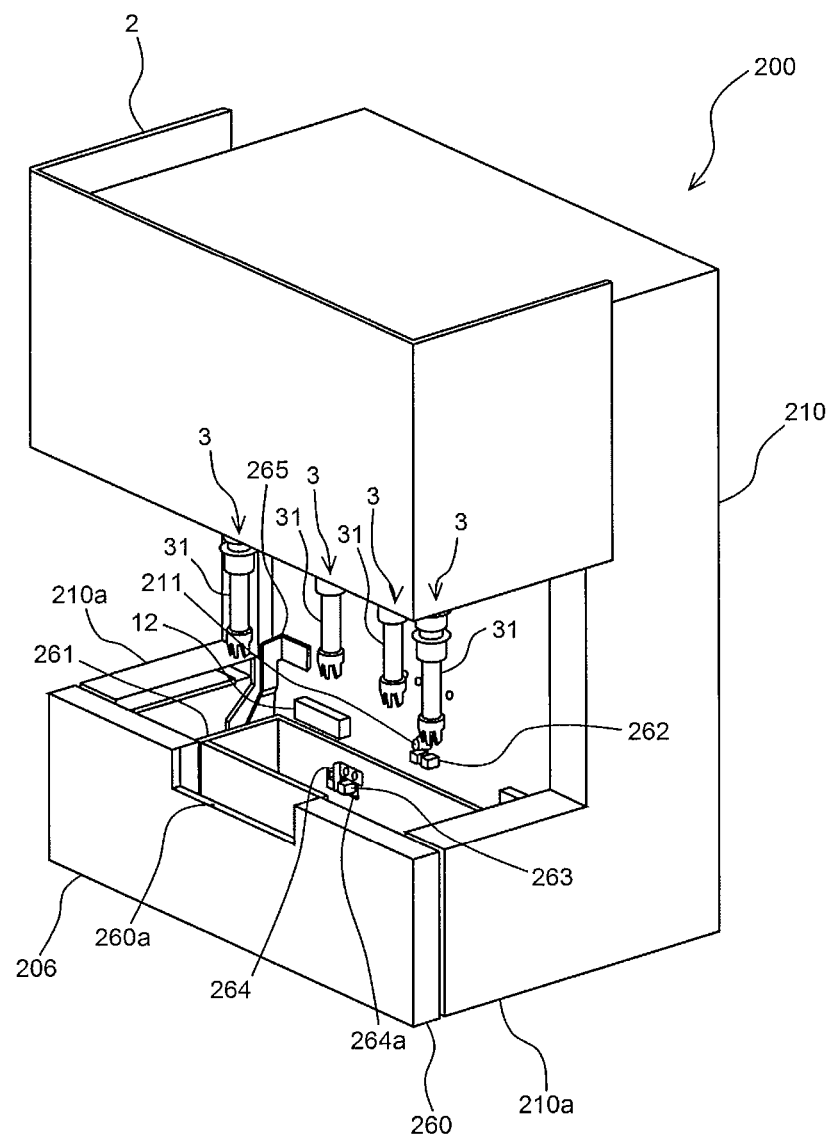
FIG. 19 is a perspective view showing the outward appearance of the homogenizer with storage cooler removed.

FIG. 19 is a perspective view showing the main body 210 when the installation section 206 is positioned at the homogenizing position without the storage cooler 204 installed. As shown in FIG. 19, the installation section 206 without the storage cooler 204 installed can be moved to from the mounting position Y to the homogenizing position X. At this time the photointerrupters 263 are respectively inserted into the two holes 264a provided on the back surface panel of the installation section 206. The detection piece 264 which is provided forward of the hole 264a is positioned in the gap between the light emitter and light receiver of the photointerrupter 263 so that the detection piece 264 blocks the light from the light emitter of the photointerrupter 263. Thus, the installation section 206 can be detected at the homogenizing position X by the photointerrupter 263.

If the storage cooler 204 is not installed, light emitted from the light emitter of the photointerrupter 262 cannot be blocked even when the installation section 206 is disposed at the homogenizing position X. That is, the photointerrupter 262 cannot detect the installation section 206 disposed at the homogenizing position X when the storage cooler 204 is not installed.

Figure 20:
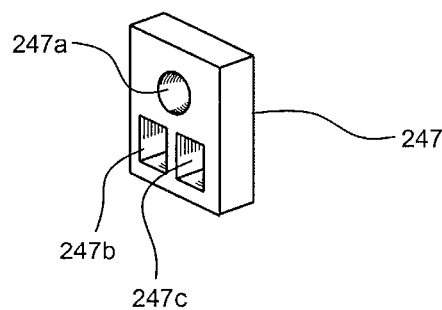
FIG. 20 is a perspective view showing the structure of the positioning block.

The structure of the storage cooler 204 is described below. As shown in FIG. 16, a positioning block 247 is provided at the lateral center of back surface of the cabinet 244. FIG. 20 is a perspective view showing the structure of the positioning block 247. The positioning block 247 has a rectangular shape, and is provided with a circular recess 247a at the top and two rectangular recesses 247b and 247c arranged side by side therebelow.

Figure 21:
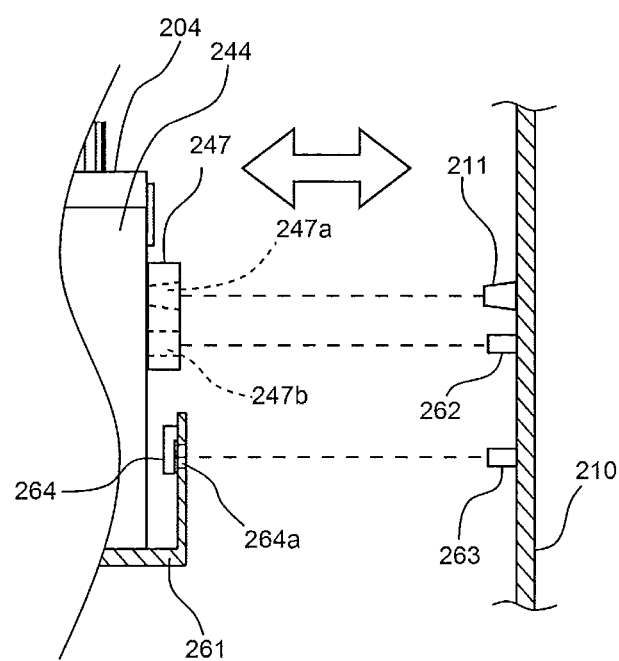
FIG. 21 is a side view schematically illustrating the movement of the installation section.

When performing the homogenizing process, the storage cooler 4 is mounted in the receiver 261 of the installation section 206 at the mounting position Y while holding the sample containers 5. Thereafter, the installation section 206 is slidably moved backward to the homogenizing position X. At this time the positioning boss 211 provided on the main body 210 is inserted into the circular recess 247a provided on the positioning block 247 so as to position the storage cooler 204. FIG. 21 is a side view schematically illustrating the movement of the installation section 206. As shown in FIG. 21, the positioning block 247 is provided on the back surface of the storage cooler 204, and the hole 264a and detection piece 264 are provided on the back surface of the receiver 261. The positioning boss 211, photointerrupter 262, and photointerrupter 263 are provided on the surface of the main body 210 facing the storage cooler 204. The magnet 12 (refer to FIG. 14) is provided on the surface of the main body 210, and a magnetic plate 48 is provided on the back surface of the storage cooler 204 so as to correspond to the magnet 12.

When the installation section 206 holding the storage cooler 204 is moved backward from the mounting position Y to the homogenizing position X, as shown in FIG. 21, at the homogenizing position X the positioning boss 211 is inserted into the circular recess 247a of the positioning block 247 on the storage cooler 204 at the homogenizing position X, the light emitter and light receiver of the photointerrupter 262 are inserted in the rectangular recesses 247b and 247c, the photointerrupter 263 is inserted in the hole 264a of the receiver 261, and the detection piece 264 is positioned between the light emitter and light receiver of the photointerrupter 263. The magnetic plate 48 is attracted to the magnet 12 at this time.

As shown in FIG. 21, the positioning boss 211 is a projection formed in a narrow taper toward the tip, and the circular recess 247a of the positioning block 247 is a frusticonical concavity which tapers toward the back. The size and angle of inclination of the positioning boss 211 and circular recess 247a are substantially identical. When the positioning boss 211 is inserted into the circular recess 247a, therefore, the inclined surface of the positioning boss 211 contacts the inclined surface of the circular recess 247a so as to position the storage cooler 204 at the proper position (position at which the homogenizer 2 is inserted in the sample container 5). Note that although the positioning boss 211 is a projection and the positioning block is a hole in the present embodiment, the inserted side and the receiving side may be reversed.

When the positioning boss 211 is inserted in the circular recess 247a as described above, the light emitter and light receiver of the photointerrupter 262 are simultaneously inserted into the rectangular recesses 247b and 247c, respectively, such that the wall between the circular recesses 247b and 247c is positioned between the light emitter and the light receiver and this wall blocks the light from the light emitter. Hence, the storage cooler 204 can be detected when installed in the installation section 206 at the homogenizing position X via the photointerrupter 262.

The installation section 206 is disposed at the homogenizing position X at this time. Therefore, the detection piece 264 which is provided forward of the hole 264a is positioned in the gap between the light emitter and light receiver of the photointerrupter 263 so that the detection piece 264 blocks the light from the light emitter of the photointerrupter 263. Thus, the installation section 206 can be detected at the homogenizing position X by the photointerrupter 263.

The storage cooler 204 is also anchored at the correct position when the magnet 12 magnetically attracts the magnetic plate 48 of the storage cooler 204. In this state, the homogenizing section 3 is inserted into the sample container 5 held in the storage cooler 204, and the homogenizing process is performed to pulverize the tissue.

Figure 22:
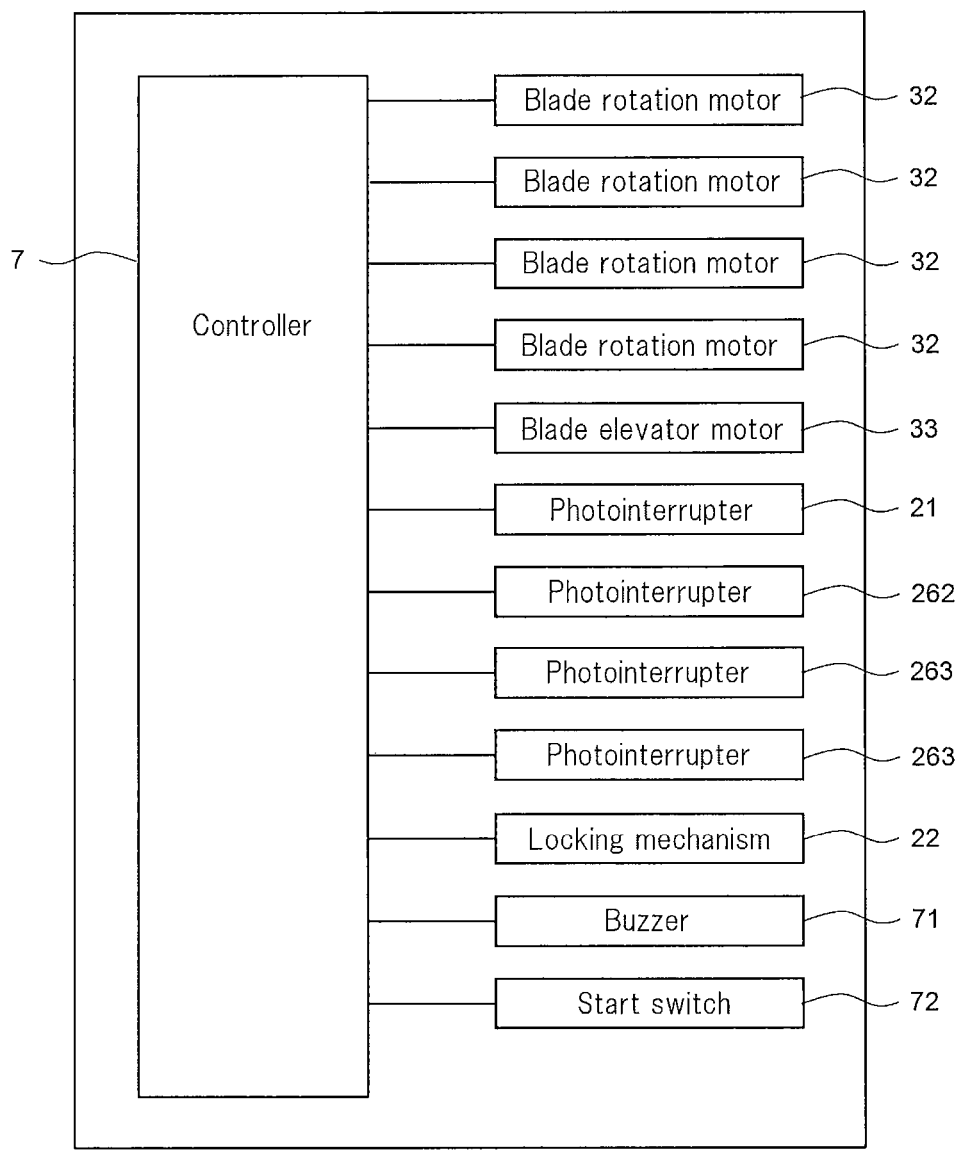
FIG. 22 is a block diagram showing the structure of the electrical circuit of the homogenizer of the second embodiment.
Figure 23:
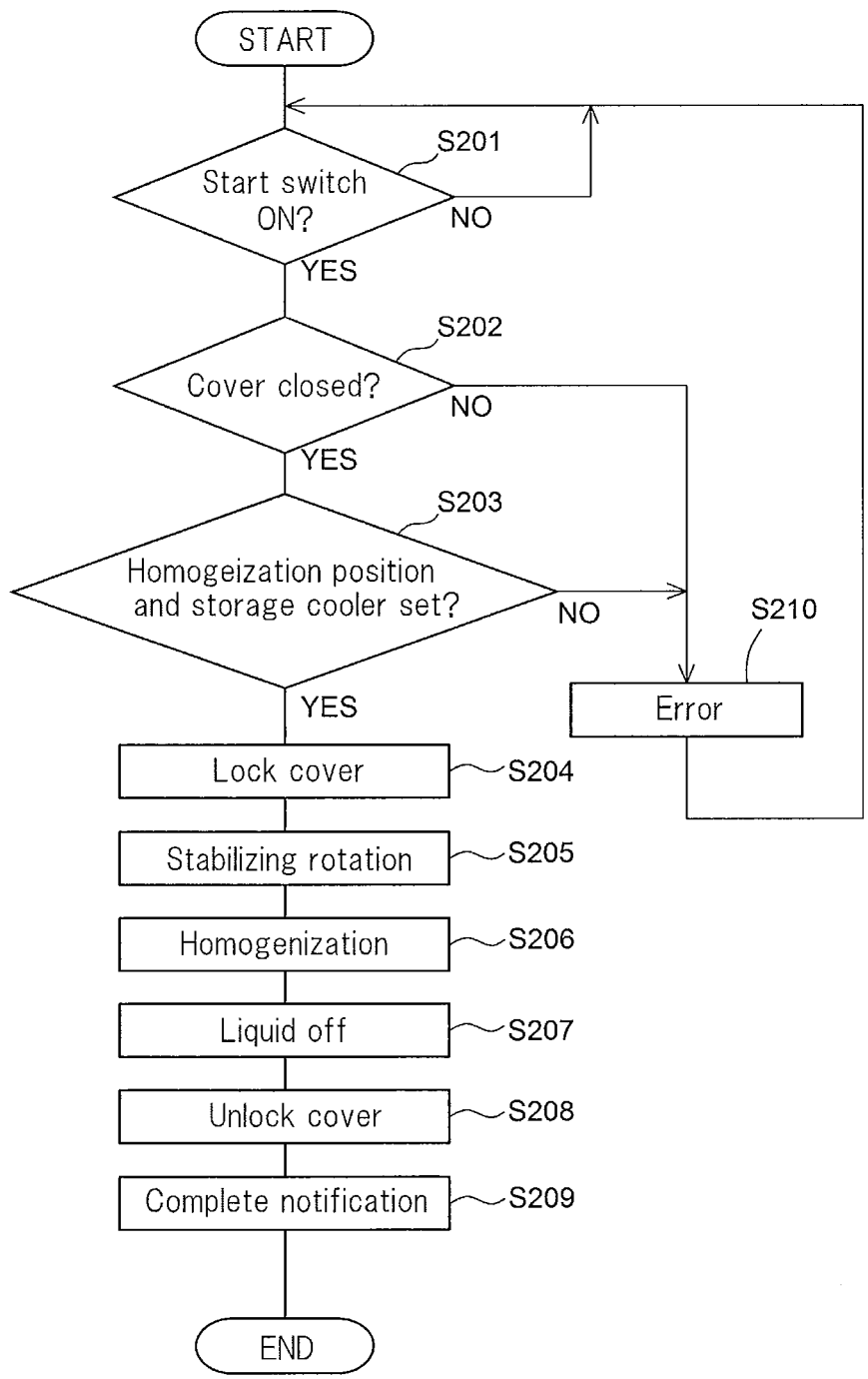
FIG. 23 is a flow chart showing the flow of the operation of the second embodiment of the homogenizer.

FIG. 22 is a block diagram showing the structure of the electrical circuit of the homogenizer 200 of the embodiment. The above photointerrupters 262 and 263 are connected to the controller 7 provided in the main body 210 of the homogenizer 200 to output detection signals to the controller 7.

The other structures of the homogenizer 200 of the present embodiment are identical to those of the homogenizer 1 of the first embodiment, and further description is therefore omitted.

Homogenizer Operation

The operation of the homogenizer 200 of the present embodiment is described below.

First, the operator opens the cover 2. The storage cooler 204 is removed from the main body 210 while the cover 2 is open. When the cover 2 is open, the operator pulls the installation section 206 forward from the homogenizing position X to the mounting position Y. The operator then removes the storage cooler 204 from the installation section 206 at the mounting position Y.

Then the operator opens the cover 244a and the inner cover 46 of the storage cooler 204, pours crushed ice into the cooling medium container 45, and covers the cooling medium container 45 with the inner cover 46. 4 mL of buffer is dispensed into the sample container 5 through the holder 46a of the inner cover 46 and the buffer is cooled. At most four sample containers 5 are prepared in this way. In this state, the arrival of tissue from the operating room is awaited.

When the tissue arrives, the operator introduces the tissue into the sample container 5 that contains the pre-cooled buffer. The operator closes the cover 244a and uses the locking mechanism 244b to lock the cover 46 in a state the sample containers 5 containing the tissue and buffer are held in the inner cover 46.

With the cover 2 of the main body 210 in an open state, the operator attaches the blender 31 to the rotation mechanism of the homogenizing section 3. At most four blenders 31 are attached to homogenizing sections 3.

After the tissue has sufficiently cooled in the storage cooler 204 outside the main body 210, the operator installs the storage cooler 204 in the receiver 261 of the installation section 206 at the mounting position Y. At this time the positioning block 247 of the storage cooler 206 is set toward the back. The operator slides the installation section 206 with the installed storage cooler 204 backward from the mounting position Y to the homogenizing position X. Thus, the positioning boss 211 is inserted into the circular recess 247a of the storage cooler 204, the light emitter and light receiver of the photointerrupter 262 are respectively inserted into the rectangular recesses 247b and 247c, and the detection piece 264 of the receiver 261 is positioned between the light emitter and light receiver of the photointerrupter 263. The magnetic plate 48 is attracted to the magnet 12 at this time. The installation of the storage cooler 204 in the main body 210 is therefore completed.

Even if the tissue in the sample container 5 is not sufficiently homogenized after homogenization is finished, without temporarily removing the storage cooler 204 from the installation section 206, it also is possible to release the locking parts 244b, open the cover 244a and remove the processed sample containers 5 to see whether the tissue in the sample container 5 is sufficiently homogenized after homogenization. And if the tissue needs to be subjected to additional homogenization, the operator can place the sample containers 5 while the storage cooler 204 is being equipped in the installation section 206. Of course, when sample container is replaced with other sample container containing a new sample (for example, containing samples cooled in another refrigerator), detaching the storage cooler 204 is not necessarily required.

The operator closes the cover 2 and presses the start switch 72 to issue an instruction to execute the tissue homogenizing process in the homogenizer 200. Note that when the cover 2 is in the open state, the cover 2 is positioned on the front surface of the start switch 72 so that the start switch 72 is hidden by the cover 2, as shown in FIG. 13. That is, the start switch 72 cannot be operated while the cover 2 is in the open state. Thus, operation of the start switch 72 is prevented while the cover 2 is open.

The controller 7 monitors the operation of the start switch 72. When the controller 7 determines that the start switch 72 has been pressed (step S201: YES), the process advances to step S202. If the start switch 72 is not pressed (step S201: NO), the controller 7 repeats the determination of step S201.

When the start switch has been pressed, the controller 72 detects whether the cover 2 is closed (step S202). Whether the cover 2 is closed is determined by the detection signal output from the photointerrupter 21. The controller 7 detects that the cover 2 is closed when the output detection signal is received. When the closed cover 2 is not detected in step S202 (step S202: NO), the controller 7 executes the error process of step S210 to alert the operator that the cover 2 is not closed. In this error process, the buzzer 71 emits a sound and the status indicator 73 flashes red indicating an error has occurred. The error process ends after a set time has elapsed, whereupon the process returns to step S201.

When the cover 2 closure is detected in step S202 (step S202: YES), the controller 7 determines whether the installation section 206 is at the homogenizing position X, and the storage cooler 204 is installed in the installation section 206 (step S203). When the storage cooler 204 is installed in the installation section 206 and the installation section 206 is moved to the homogenizing position X as described above, the photointerrupters 263 detect the installation section 206 and output a corresponding detection signal. The controller 7 detects the installation section 206 at the homogenizing position X when the detection signals are received. When the storage cooler 204 is installed in the installation section 206 and the installation section 206 is moved to the homogenizing position X as described above, the photointerrupter 262 detects the storage cooler 204 and outputs a corresponding detection signal. The controller 7 detects the installed storage cooler 204 in the main body 210 by receiving the detection signal. When the installation section 206 is not detected at the homogenizing position X or the storage cooler 204 is not detected installed in the installation section 206 (that is, detection signals are not output from any photointerrupters 262 and 263) (step S203: NO), the controller 7 executes an error process (step S210) to alert the operator that the storage cooler 204 is not properly installed.

When the installation section 206 is detected at the homogenizing position X and the storage cooler 204 is detected installed in the installation section 206 (that is, detection signals are output by all photointerrupters 262 and 263) (step S203: YES), the controller 7 locks the cover 2 (step S204) and executes the homogenizing process.

Note that the processes of steps S204 through S209 are identical to the processes of steps S4 through S209 of the first embodiment, and further description is therefore omitted.

Other Embodiments

Note that although the above embodiment is described in terms of accommodating ice as a cooling medium in the storage cooler 4 to cool the tissue and buffer in the sample container 5, the present invention is not limited to this configuration. The storage cooler also may be provided with a cooling device such as a Peltier element to cool the tissue and buffer in the sample container. In this case the storage cooler 4 may be configured with a built in secondary battery as a power source to operate the cooling device. When the storage cooler is installed in the main body, the secondary battery of the storage cooler 4 may be charged by the power source of the homogenizer 1.

Although the storage cooler 4 is configured to hold a maximum of four sample containers 5 in the above embodiment, the present invention is not limited to this number. For example, the storage cooler also may be configured to hold two or three or more than four sample containers, or the storage cooler may be configured to hold only one sample container. In this case the homogenizer is provided with the same number of homogenizing sections as the number of sample containers that can be held in the storage cooler, and the homogenizing operation is performed simultaneously for the plurality of sample containers.

Although the above embodiment is described in terms of sample containers 5 held upright in the storage cooler 4, and the homogenizing sections 3 are lowered perpendicularly to be inserted into the sample containers 5, the present invention is not limited to this configuration. The sample container may be held in the storage cooler at an inclined direction relative to the perpendicular direction, and the homogenizing section may be movable along a direction inclined at the same angle as the inclination angle of the sample container so that the homogenizing section is inserted in the inclined sample container.

Although the above embodiment is described in terms of the storage cooler 4 being removable from the main body 10 by moving the storage cooler 4 in a back-to-front direction in the main body 10, the present invention is not limited to this configuration. The storage cooler 4 also may be moved in any direction relative to the main body 10 insofar as the direction intersects the direction of movement of the homogenizing section when the homogenizing section is inserted in the sample container. For example, the homogenizer may be configured so that the storage cooler is moved laterally, or moved in an inclined direction relative to the horizontal.

The above embodiment is described in terms of the installation section being movable between the homogenizing position X and the mounting position Y so that the storage cooler 4 installed in the installation section 6 can be removed from the main body 10; however, the present invention is not limited to this configuration. For example, the homogenizer 1 may be configured with a fixed platform as an installation section used to attach and detach the storage cooler at a position below the homogenizing section, wherein the storage cooler is installed on the platform and removed from this platform to attach and detach the storage cooler in the homogenizer 1, or a slot for attaching and detaching the storage cooler may be provided as an installation section in the homogenizer so that the storage cooler is inserted and removed through this slot to make the storage cooler detachable from the homogenizer.

What is claimed is:

1. A homogenizer, for homogenizing a tissue sample collected from a living body, comprising:
    a main body; and
    a storage cooler, comprising a container holder for holding a sample container, configured to cool a tissue sample in the sample container held by the container holder, the storage cooler being detachably installed to the main body,
    wherein the main body has a blender for crushing the tissue sample in the sample container held in the storage cooler, wherein the main body comprises:
        an installation section for receiving the storage cooler set by the user; and
        a moving section configured to guide the movement of the installation section between an installing position at which the user installs the storage cooler on the installation section, and a homogenizing position at which the blender accesses in the sample container held by the storage cooler, wherein:
            the main body has a magnet and the storage cooler has a magnetic plate, and when the storage cooler is at the homogenizing position, the magnet of the main body and the magnetic plate of the storage cooler are mutually attractive.

2. The homogenizer of claim 1, wherein
    the storage cooler is configured to hold the sample container with an opening;

the blender is configured to be inserted through the opening of the sample container held by the storage cooler installed on the installation section; and the moving section guides the installation section in a direction that intersects the direction of insertion of the blender into the sample container.

3. The homogenizer of claim 1, wherein the storage cooler has an upper cover that constitutes the upper surface of the storage cooler, the main body has a restriction part that restricts an opening of the upper cover of the storage cooler installed in the installation section, the restriction part does not restrict the opening of the upper cover when the storage cooler is at the installing position, and the restriction part restricts the opening of the upper cover when the storage cooler is at the homogenizing position.

4. The homogenizer of claim 1, wherein the storage cooler has an upper cover that constitutes the upper surface of the storage cooler, the moving section is configured as capable of moving between the homogenizing position where the storage cooler is beneath the blender and the installing position where the storage cooler is positioned forward from the homogenizing position, the upper cover is rotatable around a horizontal axis provided at a back side of the upper cover, and the maximum angle of the opened upper cover is restricted such that the upper cover does not contact with the blender.

5. A homogenizer, for homogenizing a tissue sample collected from a living body, comprising:

a main body; and a storage cooler, comprising a container holder for holding a sample container, configured to cool a tissue sample in the sample container held by the container holder, the storage cooler being detachably installed to the main body, wherein the main body has a blender for crushing the tissue sample in the sample container held in the storage cooler, and the main body comprises:

a detection section for detecting the presence of the storage cooler; and a controller, wherein the controller executes the homogenizing operation to homogenize the tissue sample in the sample container by the blender when the storage cooler is detected by the detection section, and disallows an execution of the homogenizing operation by the blender when the storage cooler is not detected by the detection section.

6. The homogenizer of claim 5, wherein the main body comprises:

a cover provided on the front side of the homogenizer so as to open and close; and a cover detector for detecting the closed cover;

the controller executes the homogenizing operation by the blender when the detection section detects the storage cooler and the cover detector detects the closed cover, and disallows an execution of the homogenizing operation by the blender when the storage cooler is not detected by the detection section or the cover detector does not detect the closed cover.

7. The homogenizer of claim 6, wherein the main body comprises:

an instruction section for issuing an instruction to start the homogenizing operation by the blender; and a locking mechanism to lock the cover;

when the detection section detects the storage cooler and the cover detector detects the closed cover and the instruction section issues an instruction to start the homogenizing operation, the controller locks the cover by the locking mechanism, executes the homogenizing operation by the blender, and unlocks the cover by the locking mechanism after the homogenizing operation ends.

8. The homogenizer of claim 7, wherein the cover is positioned at a front of the blender when closed and is positioned at a front of the instruction section when opened.

9. The homogenizer of claim 5, wherein the blender has a blade that is rotatable on an axis along which the blender is inserted to the sample container, and is configured to homogenize the tissue sample by rotating the blade while in contact with the tissue sample in the sample container, and the controller inserts the blender into the sample container held by the storage cooler and rotates the blade to homogenize the tissue sample in the sample container, then moves the blender in a direction adjacent to the opening of the sample container and again rotates the blade to remove the tissue sample adhered to the blade.

10. The homogenizer of claim 5, wherein the storage cooler is configured to hold a plurality of sample containers, and the main body has the same number of blenders as the number of sample containers that can be held by the storage cooler.

11. The homogenizer of claim 5, wherein the main body comprises a cover provided on the front side of the homogenizer so as to open and close, and the storage cooler can be installed on the main body when the cover is open, and is configured to not be installed on the main body when the cover is closed.

12. The homogenizer of claim 11, wherein the blender hangs down in the main body, the storage cooler is installed in the main body by sliding front to back under the blender, and the cover is opened and closed by sliding vertically.

13. The homogenizer of claim 5, wherein the storage cooler comprises a cabinet to internally accommodate a cooling medium.

14. The homogenizer of claim 13, wherein the storage cooler has an opening to allow access for the blender into the sample container held in the cabinet.

15. The homogenizer of claim 14, wherein the storage cooler has a cylindrical part that protrudes around the opening.

16. The homogenizer of claim 13, wherein the storage cooler is provided with a detachable inner cover that covers the cooling medium accommodated therein, and an outer cover that opens and closes on the top surface of the storage cooler.

17. A homogenizer, for homogenizing a tissue sample collected from a living body, comprising:

a storage cooler including a container holder for holding a sample container with cooling, and a main body on which the storage cooler is detachably equipped, wherein the main body includes:

a blender that homogenizes a tissue sample in the sample container held by the container holder;

a detector that detects the equipped storage cooler;
an instruction receiver that receives an instruction to start a homogenization; and
a controller for controlling the operation of the blender,
the controller disallows an execution of the homogenization when the detector does not detects the equipped storage cooler, even if the instruction to start is received.

* * * * *